US010730902B2

(12) United States Patent
Zetterberg et al.

(10) Patent No.: US 10,730,902 B2
(45) Date of Patent: Aug. 4, 2020

(54) 1,1'-SULFANEDIYL-DI-BETA-D-GALACTOPYRANOSIDES AS INHIBITORS OF GALECTINS

(71) Applicant: GALECTO BIOTECH AB, Copenhagen (DK)

(72) Inventors: Fredrik Zetterberg, Askim (SE); Ulf Nilsson, Lund (SE); Hakon Leffler, Lund (SE); Anders Pedersen, Lyngby (DK); Hans Schambye, Virum (DK); Thomas Brimert, Blentarp (SE); Richard Johnsson, Staffanstorp (SE)

(73) Assignee: GALECTO BIOTECH AB, Copenhagen (DK)

( * ) Notice: Subject to any disclaimer, the term of this patent is extended or adjusted under 35 U.S.C. 154(b) by 0 days.

(21) Appl. No.: 15/774,868

(22) PCT Filed: Nov. 8, 2016

(86) PCT No.: PCT/EP2016/076918
§ 371 (c)(1),
(2) Date: May 9, 2018

(87) PCT Pub. No.: WO2017/080973
PCT Pub. Date: May 18, 2017

(65) Prior Publication Data
US 2018/0327440 A1    Nov. 15, 2018

(30) Foreign Application Priority Data

Nov. 9, 2015 (EP) .................................. 15193657
Jun. 1, 2016 (EP) .................................. 16172358

(51) Int. Cl.
*C07H 19/056* (2006.01)
*A61P 27/02* (2006.01)

(52) U.S. Cl.
CPC ............ *C07H 19/056* (2013.01); *A61P 27/02* (2018.01)

(58) Field of Classification Search
CPC ................................ C07H 19/056; A61P 27/02
See application file for complete search history.

(56) References Cited

U.S. PATENT DOCUMENTS 7,700,763 B2      4/2010  Leffler et al.
2014/0011765 A1*  1/2014  Nilsson .................. C07H 5/10
                                                      514/53

FOREIGN PATENT DOCUMENTS

| WO | 2009/139719 A1 | 11/2009 |
| WO | 2014/067986 A1 | 5/2014 |
| WO | 2016/005311 A1 | 1/2016 |
| WO | 2016/113335 A1 | 7/2016 |

OTHER PUBLICATIONS

Certified copy of foreign priority document EPO 16172358.0 as published by WIPO, https://patentscope.wipo.int, accessed online on Aug. 14, 2019. (Year: 2017).*
International Search Report dated Dec. 21, 2016 of corresponding International application No. PCT/EP2016/076918; 5 pgs.
Bader A. Salameh, et al., "1H-1,2,3-Triazol-1-yl thiodigalactoside derivatives as high affinity galectin-e inhibitors", Bioorganic & Medicinal Chemistry, Pergamon, GB vol. 18, No. 14, Jul. 15, 2010; pp. 5369-5370.
Indian Office Action dated Nov. 29, 2019, in connection with corresponding IN Application No. 201817014003 (6 pgs.).

* cited by examiner

*Primary Examiner* — Jonathan S Lau
(74) *Attorney, Agent, or Firm* — Maier & Maier, PLLC

(57) ABSTRACT

The present invention relates to a compound of the general formula. The compound of formula is suitable for use in a method for treating a disorder relating to the binding of a galectin, such as galectin-3 to a ligand in a mammal, such as a human. Furthermore, the present invention concerns a method for treatment of a disorder relating to the binding of a galectin, such as galectin-3 to a ligand in a mammal, such as a human.

20 Claims, No Drawings

1,1'-SULFANEDIYL-DI-BETA-D-GALACTOPYRANOSIDES AS INHIBITORS OF GALECTINS

TECHNICAL FIELD

The present invention relates to novel compounds, the use of said compounds as medicament and for the manufacture of a medicament for the treatment of a mammal suffering from inflammation; fibrosis, such as pulmonary fibrosis, liver fibrosis, kidney fibrosis, ophthalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization. The invention also relates to pharmaceutical compositions comprising said novel compounds.

BACKGROUND ART

Galectins are proteins with a characteristic carbohydrate recognition domain (CRD) (Leffler et al., 2004). This is a tightly folded β-sandwich of about 130 amino acids (about 15 kDa) with the two defining features 1) a β-galactose binding site and 2) sufficient similarity in a sequence motif of about seven amino acids, most of which (about six residues) make up the β-galactose binding site. However, sites adjacent to the β-galactose site are required for tight binding of natural saccharides and different preferences of these give galectins different fine specificity for natural saccharides.

The recent completion of the human, mouse and rat genome sequences reveal about 15 galectins and galectin-like proteins in one mammalian genome with slight variation between species (Leffler et al., 2004).

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Lepur et al., 2012). These were the first discovered galectins and are abundant in many tissues.

There are now over 5700 publications on galectins in PubMed, with most, as mentioned above, about galectins-1 (>1400) and -3 (>2800). Strong evidence suggests roles for galectins in e.g. inflammation and cancer, and development (Blidner et al., 2015, Ebrahim et al., 2014).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway, as yet unknown, but possibly similar to the export of e.g. IL-1 (Leffler et al., 2004; Arthur et al., 2015). They can also function in all these compartments; for galectin-3, solid evidence published in well respected journals support roles in RNA splicing in the nucleus, inhibition of apoptosis in the cytosol, accumulation around disrupted vesicles, association with microtubule organizing center of cilia, and a variety of extracellular effects on cell signaling and adhesion (Elola et al. 2015, Funasaka et al., 2014, Aits et al., 2015, Clare et al., 2014). Other galectins also may act in the cytosol by enhancing apoptosis and regulating the cell cycle and differentiation in certain cells. Most galectins act also extracellularly by cross-linking glycoproteins (e.g. laminin, integrins, and IgE receptors) possibly forming supramolecular ordered arrays (Elola et al., 2015) and may thereby modulate cell adhesion and induce intracellular signals. Related to this, recent years have seen the emergence of a molecular mechanism of these galectin functions involving a formation of microdomains (lattices) within membranes, (Elola et al., 2015) which in turn affects intracellular trafficking and cell surface presentation of glycoprotein receptors. This has been documented in cell culture, in null mutant mice, and animals treated with galectin or galectin inhibitors.

Potential Therapeutic Use of Galectin-3 Inhibitors

Galectin-3 has been implicated in diverse phenomena and, hence, inhibitors may have multiple uses (Blanchard et al., 2014). It is easy to perceive this as a lack of specificity or lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation

A pro-inflammatory role of galectin-3 is indicated by its induction in cells at inflammatory sites, a variety of effects on immune cells (e.g. oxidative burst in neutrophils and chemotaxis in monocytes), and decrease of the inflammatory response, mainly in neutrophils and macrophages, in null mutant mice (Blidner et al., 2015, Arthur et al., 2015). Importantly, recent studies have identified galectin-3 as a key rate-limiting factor in macrophage M2 differentiation and myofibroblast activation, which influences the development of fibrosis (Mackinnon et al., 2008; Mackinnon et al., 2012; Li et al., 2014).

Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition to the arsenal available for this.

Treatment of Fibrosis-Related Conditions

The idea of a possible role of galectin-3 in fibrosis comes from cell and ex vivo studies on macrophage differentiation (Mackinnon et al., 2008), as well as from in vivo studies on macrophage differentiation and myofibroblast activation (Mackinnon et al., 2012). Briefly, the hypothesis is as follows: Galectin-3 has been shown to prolong cell surface residence and thus enhance responsiveness of certain receptors (Elola et al., 2015), such as the TGF-β receptor (MacKinnon, 2012), which in turn regulates alternative macrophage differentiation into M2 macrophages and myofibroblast activation. Hence, as galectin-3 is a good candidate for being an endogenous enhancer of TGF-β signaling and alternative macrophage differentiation and myofibroblast activation, galectin-3 inhibitors may be very useful in treating fibrosis and adverse tissue remodeling.

Treatment of Cancer

A large number of immunohistochemical studies show changed expression of certain galectins in cancer (Thijssen et al, 2015; Ebrahim et al., 2014) and for example galectin-3 is now an established histochemical marker of thyroid cancer. The direct evidence for a role of galectin-3 in cancer comes mainly from mouse models. In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. Further, recent evidence have shown that galectin-3 plays a critical role in the tumor microenvironment (Ruvolo, 2015). Galectin-3 is also believed to regulate the interaction between the tumor cells and immune cells, such as T-lymphocytes (T-cells), and inhibition of galectin-3 has been shown to restore T-cell activity (Demotte et al. 2010, Kouo et al. 2015, Menero et al. 2015). From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). More recently, inhibition of galectin-3 with small molecules have been demonstrated to indeed greatly enhance tumor cell sensitivity towards radiation and standard pro-apoptotic drugs in cell assays and ex vivo (Blanchard et al., 2015).

Also other galectins are frequently over-expressed in low differentiated cancer cells, or induced in specific cancer types (Thijssen et al, 2015; Ebrahim et al., 2014). Galectin-1 induces apoptosis in activated T-cells and has a remarkable immunosuppressive effect on autoimmune disease in vivo (Blidner et al., 2015). Therefore, the over-expression of these galectins in cancers might help the tumor to defend itself against the T-cell response raised by the host.

Null mutant mice for galectins-1, -3, -7 and -9 have been established and are healthy and reproduce apparently normally in animal house conditions. However, further studies have revealed subtle phenotypes under different type of challenge, mainly in function of immune cells (Blidner et al., 2015), but also other cells types (Viguier et al., 2014). The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Treatment of Angiogenesis

Vascular endothelial growth factors (VEGFs) signaling through VEGF receptor-2 (VEGFR-2) is the primary angiogenic pathway. Studies have been published demonstrating that both galectin-1 (Gal-1) and galectin-3 (Gal-3) are important modulators for VEGF/VEGFR-2 signaling pathway (Croci et al., 2014). It has also been published that a galectin inhibitor, TDX, is expected have efficacy against pathological angiogenesis. (Chen 2012)

Known Inhibitors

Natural Ligands

Solid phase binding assays and inhibition assays have identified a number of saccharides and glycoconjugates with the ability to bind galectins (Leffler et al., 2004; Elola et al., 2015). All galectins bind lactose with a $K_d$ of 0.5-1 mM. The affinity of D-galactose is 50-100 times lower. N-Acetyllactosamine and related disaccharides bind about as well as lactose, but for certain galectins, they can bind either worse or up to 10 times better. The best small saccharide ligands for galectin-3 were those carrying blood group A-determinants attached to lactose or LacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1. Modified plant pectin polysaccharides or galactomannans, isolated as inclompletely defined mixtures, have been reported to bind galectins (Glinsky and Raz, 2009), but the mechanism and affinity remains uncertain.

The above-described natural saccharides that have been identified as galectin-3 ligands are not suitable for use as active components in pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler, 2004, Elola et al., 2015). These longer saccharides were characterized by having an additional sugar residue added to the C-3 position of galactose (in e.g. lactose or LacNAc) that bound an extended binding groove. The shape of this groove varies between galectins, suggesting that the same extensions would not be bound equally by the different galectins.

Synthetic Inhibitors

Saccharides coupled to amino acids with anti-cancer activity were first identified as natural compounds in serum, but subsequently, synthetic analogues have been made (Glinsky et al., 1996). Among them, those with lactose or galactose coupled to the amino acid inhibit galectins, but only with about the same potency as the corresponding underivatized sugar. A modified forms of citrus pectins (Glinsky and Raz, 2009) that may inhibit galectin-3 shows anti-tumor activity in vivo.

Cluster molecules with multiple lactose moieties sometimes showed a strong multivalency effect when binding to galectins, but other times not (Wolfenden et al., 2015) The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune responses in patients. Furthermore, they are susceptible to acidic hydrolysis in the stomach and to enzymatic hydrolysis. Thus, there is a need for small synthetic molecules Thiodigalactoside is known to be a synthetic and hydrolytically stable, yet polar inhibitor, approximately as efficient as N-acetyllactosamine N-Acetyllactosamine derivatives carrying aromatic amides or substituted benzyl ethers at C-3' have been demonstrated to be highly efficient inhibitors of galectin-3, with unprecedented $IC_{50}$ values as low as 4.8 μM, which is a 20-fold improvement in comparison with the natural N-acetyllactosamine disaccharide (Sörme et al., 2002; Sörme et al., 2003b). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, the C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-diamido- or 3,3'-ditriazolyl-derivatization of thiodigalactoside have been developed, (Cumpstey et al., 2005b; Cumpstey et al., 2008; Salameh et al., 2010; WO/2005/113569 and US2007185041; WO/2005/113568, U.S. Pat. No. 7,638,623 B2; T. Delaine et. al., 2016; WO2016005311; WO2016113335) which lack O-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise a disadvantage in their multistep synthesis involving double inversion reaction to reach at 3-N-derivatized galactose building blocks. Furthermore, cyclohexane replacement of one galactose ring in thiodigalactoside has been evidenced to mimic the galactose ring and hence to provide galectin-1 and -3 inhibitors with efficiency approaching those of the diamido- and ditriazolyl-thiodigalactoside derivatives (WO/2010/126435). Replacement of a D-galactopyranose unit with a substituted cyclohexane decreases polarity and most likely also metabolic susceptibility, thus improving drug-like properties.

Some earlier described compounds have the following general formulas

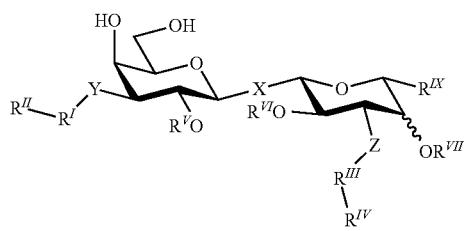

as described in WO/2005/113568, and

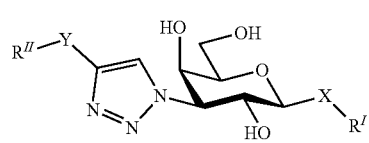

as described in WO/2005/113569, in which $R^1$ can be a D-galactose, and

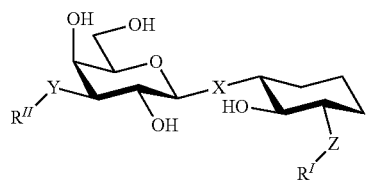

as described in WO/2010/126435.

Thus, due to the less than optimal manufacturing processes towards galactose 3-N-derivatization (Z and Y are preferably nitrogen atoms) involving double inversion reactions at a complex protected D-galactopyranose derivative of the compounds of the prior art, there is still a considerable need within the art of inhibitors against galectins, in particular of galectin-1 and galectin-3.

In recently published US20140099319, WO2014067986 and T. Delaine et. al., 2016 are disclosed a compound of formula

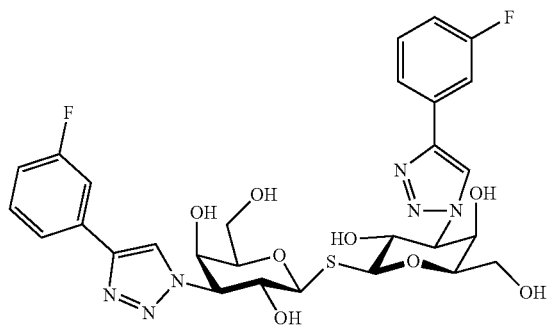

having fluorine in the meta position on both the phenyl rings in relation to the triazole rings. This compound has been shown to be a promising drug candidate for lung fibrosis, and in particular is very selective on galectin-3 with high affinity.

Recently a new class high affinity α-D-galactopyranoses of the general structure

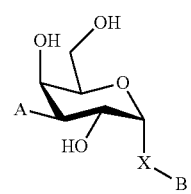

were disclosed in WO2016120403. Some of these compounds have good in vitro PK properties which translated into high oral bioavailability.

SUMMARY OF THE INVENTION

The compounds of the present invention have very high affinity for Gal-3 and high selectivity for Gal-3 over Gal-1, and are considered potent drug candidates. These compounds also have high solubility, which is important for making pharmaceutical formulations, in particular pulmonary and ocular formulations.

In a broad aspect the present invention relates to a 1,1'-sulfanediyl-di-β-D-galacto-pyranoside compound of formula (1)

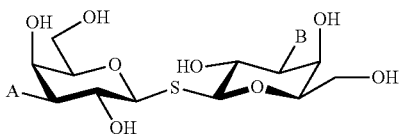

wherein A is selected from a group of formula 2

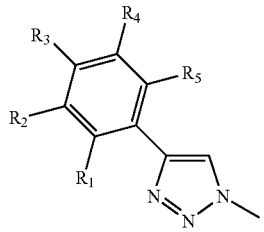

Wherein $R_1$-$R_5$ are independently selected from H; Cl; Br; I; F; methyl optionally substituted with a fluorine (F); $R_7$O-, wherein $R_7$ is selected from $C_{1-3}$ alkyl optionally substituted with a F; $NH_2$, OH; CN; $NH_2$-$COR_8$, wherein $R^8$ is selected from $C_{1-3}$ alkyl optionally substituted with a F; and $OCH_3$ optionally substituted with a F; and B is selected from a group of formula 3

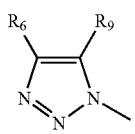

wherein $R_6$ and $R_9$ are independently selected from
H; Cl; Br; I; F; $NR_{10}R_{11}$; $OR_{12}$; C(=O)—$R_{13}$; CN; O(C=O)—$R_{16}$; NH(C=O)—$R_{17}$; C(=O)—$OR_{21}$; C(=O)—$NR_{22}R_{23}$; $SR_{18}$; S(=O)—$R_{19}$; $SO_2R_{20}$;

$C_{1-10}$alkyl, optionally substituted with a group selected from F; Oxo; $NR_{14}R_{15}$; $OR_{24}$; C(=O)—$R_{25}$; CN; O(C=O)—$R_{26}$; NH(C=O)—$R_{27}$; C(=O)—$OR_{28}$; C(=O)—$NR_{29}R_{30}$; $SR_{31}$; S(=O)—$R_{32}$; $SO_2R_{33}$;

$C_{3-7}$ cycloalkyl, optionally substituted with a group selected from F; Oxo; $NR_{34}R_{35}$; $OR_{36}$; C(=O)—$R_{37}$; CN; O(C=O)—$R_{38}$; NH(C=O)—$R_{39}$; C(=O)—$OR_{40}$; C(=O)—$NR_{41}R_{42}$, $SR_{43}$; S(=O)—$R_{44}$; $SO_2R_{45}$; and $C_{1-4}$ alkyl optionally substituted with a F;

branched $C_{3-10}$ alkyl, optionally substituted with a group selected from F; Oxo; $NR_{46}R_{47}$; $OR_{48}$; C(=O)—$R_{49}$; CN; O(C=O)—$R_{50}$; NH(C=O)—$R_{51}$; C(=O)—$OR_{52}$; C(=O)—$NR_{53}R_{54}$; $SR_{55}$; S(=O)—$R_{56}$; $SO_2R_{57}$; and $C_{1-4}$ alkyl optionally substituted with a F;

a 4-7-membered heterocyclic group being saturated or unsaturated and having 1-3 hetero atoms and 3-6 carbon atoms, optionally substituted with a $C_{1-4}$ alkyl optionally substituted with a F; Oxo; $NR_{58}R_{59}$; $OR_{60}$; C(=O)—$R_{61}$; CN; O(C=O)—$R_{62}$; NH(C=O)—$R_{63}$, $SR_{64}$; S(=O)—$R_{65}$; and $SO_2R_{66}$;

wherein $R_{10}$-$R_{66}$ are independently selected from:
H;
$C_{1-10}$ alkyl optionally substituted with a group selected from F, oxo, CN, $OCH_3$, $OCF_3$, $OCH_2CH_3$, optionally substituted with a F, and $SCH_2CH_3$, optionally substituted with a group selected from F, $SCH_3$, $SCF_3OCH_3$, and $OCF_3$;

$C_{3-7}$ cycloalkyl optionally substituted with a group selected from F, oxo, CN, $OCH_3$, $OCF_3$, $OCH_2CH_3$, optionally substituted with a F, and $SCH_2CH_3$, optionally substituted with a group selected from F, $SCH_3$, $SCF_3OCH_3$, and $OCF_3$;

branched $C_{3-10}$ alkyl, optionally substituted with a group selected from F, oxo, CN, $OCH_3$, $OCF_3$, $OCH_2CH_3$, optionally substituted with a F, and $SCH_2CH_3$, optionally substituted with a group selected from F, $SCH_3$, $SCF_3OCH_3$, and $OCF_3$;

4-7-membered heterocyclic group being saturated or unsaturated and having 1-3 hetero atoms and 3-6 carbon atoms optionally substituted with a group selected from F, oxo, CN, $OCH_3$, $OCF_3$, $OCH_2CH_3$, optionally substituted with a F, and $SCH_2CH_3$, optionally substituted with a group selected from F, $SCH_3$, $SCF_3OCH_3$, and $OCF_3$;

$OC_{1-10}$alkyl optionally substituted with a group selected from F, oxo, CN, $OCH_3$, $OCF_3$, $OCH_2CH_3$, optionally substituted with a F, and $SCH_2CH_3$, optionally substituted with a group selected from F, $SCH_3$, $SCF_3OCH_3$, and $OCF_3$;

$OC_{3-7}$cycloalkyl optionally substituted with a group selected from F, oxo, CN, $OCH_3$, $OCF_3$, $OCH_2CH_3$, optionally substituted with a F, and $SCH_2CH_3$, optionally substituted with a group selected from F, $SCH_3$, $SCF_3OCH_3$, and $OCF_3$;

O-(4-7-membered heterocyclic group being saturated or unsaturated and having 1-3 hetero atoms and 3-6 carbon atoms) optionally substituted with a group selected from F, oxo, CN, $OCH_3$, $OCF_3$, $OCH_2CH_3$, optionally substituted with a F, and $SCH_2CH_3$, optionally substituted with a group selected from F, $SCH_3$, $SCF_3$ $OCH_3$, and $OCF_3$;

$NHC_{1-10}$ alkyl optionally substituted with a group selected from F, oxo, CN, $OCH_3$, $OCF_3$, $OCH_2CH_3$, optionally substituted with a F, and $SCH_2CH_3$, optionally substituted with a group selected from F, $SCH_3$, $SCF_3OCH_3$, and $OCF_3$;

$NHC_{3-7}$cycloalkyl optionally substituted with a group selected from F, oxo, CN, $OCH_3$, $OCF_3$, $OCH_2CH_3$, optionally substituted with a F, and $SCH_2CH_3$, optionally substituted with a group selected from F, $SCH_3$, $SCF_3$ $OCH_3$, and $OCF_3$; or NH-(4-7-membered heterocyclic group being saturated or unsaturated and having 1-3 hetero atoms and 3-6 carbon atoms) optionally substituted with a group selected from F, oxo, CN, $OCH_3$, $OCF_3$, $OCH_2CH_3$, optionally substituted with a F, and $SCH_2CH_3$, optionally substituted with a group selected from F, $SCH_3$, $SCF_3$ $OCH_3$, and $OCF_3$;

or a pharmaceutically acceptable salt or solvate thereof.

In another aspect the present invention relates to a 1,1'-sulfanediyl-di-β-D-galacto-pyranoside compound of formula (1)

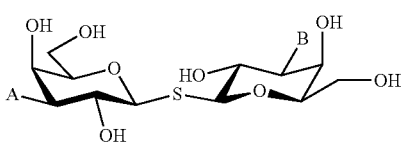

wherein A is selected from a group of formula 2

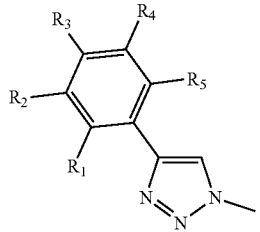

(2)

Wherein $R_1$-$R_5$ are independently selected from H; Cl; Br; I; F; methyl optionally substituted with a fluorine (F); $R_7O$—, wherein $R_7$ is selected from $C_{1-3}$ alkyl optionally substituted with a F; $NH_2$; OH; CN; $NH_2$—$COR_8$, wherein $R_8$ is selected from $C_{1-3}$ alkyl optionally substituted with a F; and $OCH_3$ optionally substituted with a F; and
B is selected from a group of formula 3

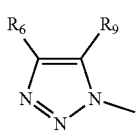

(3)

wherein $R_6$ and $R_9$ are independently selected from H; Cl; Br; I; F; $NR_{10}R_{11}$; $OR_{12}$; C(=O)—$R_{13}$; CN; O(C=O)—$R_{16}$; NH(C=O)—$R_{17}$; $C_{1-10}$ alkyl, optionally substituted with a group selected from $OCH_3$, $OCF_3$, $NR_{14}R_{15}$, CN, and F; $C_{3-7}$ cycloalkyl, optionally substituted with a $C_{1-4}$ alkyl optionally substituted with a F; branched $C_{3-19}$ alkyl, optionally substituted with a $C_{1-4}$ alkyl optionally substituted with a F; a 4-7-membered heterocyclic group being saturated or unsaturated and having 1-3 hetero atoms and 3-6 carbon atoms, optionally substituted with a $C_{1-4}$ alkyl optionally substituted with a F; Oxo; and O—$C_{1-3}$ alkyl optionally substituted with a F;
wherein $R_{10}$, $R_{11}$, $R_{12}$, $R_{14}$, and $R_{15}$ are independently selected from H; $C_{1-10}$ alkyl optionally substituted with a group selected from F, CN, $OCH_3$, or $OCF_3$; $C_{3-7}$ cycloalkyl optionally substituted with a group selected from F, CN, $OCH_3$, or $OCF_3$; or 4-7-membered heterocyclic group being saturated or unsaturated and having 1-3 hetero atoms and 3-6 carbon atoms optionally substituted with a group selected from F, CN, $OCH_3$, or $OCF_3$;
wherein $R_{13}$ is selected from H; $C_{1-10}$ alkyl optionally substituted with a group selected from F, CN, $OCH_3$, or $OCF_3$; $C_{3-7}$ cycloalkyl optionally substituted with a group selected from F, CN, $OCH_3$, or $OCF_3$; 4-7-membered heterocyclic group being saturated or unsaturated and having 1-3 hetero atoms and 3-6 carbon atoms optionally substituted with a group selected from F, CN, $OCH_3$, or $OCF_3$; $OC_{1-10}$alkyl optionally substituted with a group selected from F, CN, $OCH_3$, or $OCF_3$; $OC_{3-7}$cycloalkyl optionally substituted with a group selected from F, CN, $OCH_3$, or $OCF_3$; O-(4-7-membered heterocyclic group being saturated or unsaturated and having 1-3 hetero atoms and 3-6 carbon atoms) optionally substituted with a group selected from F, CN, $OCH_3$, or $OCF_3$; $NHC_{1-10}$ alkyl optionally substituted with a group selected from F, CN, $OCH_3$, or $OCF_3$; $NHC_{3-7}$cycloalkyl optionally substituted with a group selected from F, CN, $OCH_3$, or $OCF_3$; or NH-(4-7-membered heterocyclic group being saturated or unsaturated and having 1-3 hetero atoms and 3-6 carbon atoms) optionally substituted with a group selected from F, CN, $OCH_3$, or $OCF_3$;
wherein $R_{16}$ is selected from $C_{1-10}$ alkyl optionally substituted with a group selected from F, CN, $OCH_3$, or $OCF_3$; $C_{3-7}$ cycloalkyl optionally substituted with a group selected from F, CN, $OCH_3$, or $OCF_3$; or 4-7-membered heterocyclic group being saturated or unsaturated and having 1-3 hetero atoms and 3-6 carbon atoms optionally substituted with a group selected from F, CN, $OCH_3$, or $OCF_3$,
wherein $R_{17}$ is selected from $C_{1-10}$ alkyl optionally substituted with a group selected from F, CN, $OCH_3$, or $OCF_3$; $C_{3-7}$ cycloalkyl optionally substituted with a group selected from F, CN, $OCH_3$, or $OCF_3$; or 4-7-membered heterocyclic group being saturated or unsaturated and having 1-3 hetero atoms and 3-6 carbon atoms optionally substituted with a group selected from F, CN, $OCH_3$, or $OCF_3$,
or a pharmaceutically acceptable salt or solvate thereof.

In another aspect the present invention relates to a compound of formula (1) for use as a medicine.

In a further aspect the present invention relates to a pharmaceutical composition comprising the compound of formula (1) and optionally a pharmaceutically acceptable additive, such as carrier or excipient.

In a still further aspect the present invention relates to a compound of formula (1) for use in a method for treating a disorder relating to the binding of a galectin, such as galectin-1 and galectin-3 to a ligand in a mammal, such as a human.

In a further aspect the present invention relates to a method for treatment of a disorder relating to the binding of a galectin, such as galectin-1 and galectin-3, to a ligand in a mammal, such as a human, wherein a therapeutically effective amount of at least one compound of formula (1) is administered to a mammal in need of said treatment.

In a still further aspect the present invention relates to a process of preparing a compound of formula 1 or a pharmaceutically acceptable salt or solvate thereof comprising the steps a1 to a10 as described herein below.

In a further aspect the present invention also relates to a composition comprising hydroxyethyl cellulose (HEC) and a drug for treatment of an eye disease, disorder or condition.

In a still further aspect the present invention also relates to a composition comprising hydroxyethyl cellulose (HEC) and a galectin inhibitor for use in a method for treatment of ocular angiogenesis or ocular fibrosis, such as for treatment of proliferative vitreoretinopathy.

In a still further aspect the present invention also relates to an aqueous composition comprising HEC and a galectin inhibitor. Such aqueous composition may be suitable for topical or injection administration to the eyes of a mammal.

Further aspects of the invention are described below.

DETAILED DESCRIPTION OF THE INVENTION

In an aspect the present invention relates to a 1,1'-sulfanediyl-di-β-D-galactopyranoside compound of formula (1)

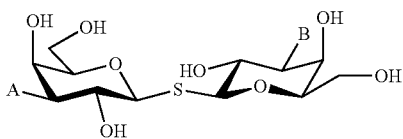

Wherein A is selected from a group of formula 2

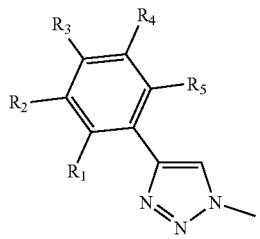

Wherein R₁-R₅ are independently selected from H; Cl; Br; I; F; methyl optionally substituted with a fluorine (F); R₇O—, wherein R₇ is selected from C₁₋₃ alkyl optionally substituted with a F; NH₂; OH; CN; NH₂—COR₈, wherein R₈ is selected from C₁₋₃ alkyl optionally substituted with a F; and OCH₃ optionally substituted with a F; and B is selected from a group of formula 3

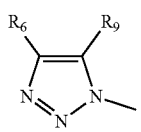

wherein $R_6$ and $R_9$ are independently selected from H; Cl; Br; I; F; $NR_{10}R_{11}$; $OR_{12}$; C(=O)—$R_{13}$; CN; O(C=O)—$R_{16}$; NH(C=O)—$R_{17}$; $C_{1-10}$ alkyl, optionally substituted with a group selected from $OCH_3$, $OCF_3$, $NR_{14}R_{15}$, CN, and F; $C_{3-7}$ cycloalkyl, optionally substituted with a $C_{1-4}$ alkyl optionally substituted with a F; branched $C_{3-10}$ alkyl, optionally substituted with a $C_{1-4}$ alkyl optionally substituted with a F; a 4-7-membered heterocyclic group being saturated or unsaturated and having 1-3 hetero atoms and 3-6 carbon atoms, optionally substituted with a $C_{1-4}$ alkyl optionally substituted with a F; Oxo; and O—$C_{1-3}$ alkyl optionally substituted with a F;

wherein $R_{10}$, $R_{11}$, $R_{12}$, $R_{14}$, and $R_{15}$ are independently selected from H; $C_{1-10}$ alkyl optionally substituted with a group selected from F, CN, $OCH_3$, or $OCF_3$; $C_{3-7}$ cycloalkyl optionally substituted with a group selected from F, CN, $OCH_3$, or $OCF_3$; or 4-7-membered heterocyclic group being saturated or unsaturated and having 1-3 hetero atoms and 3-6 carbon atoms optionally substituted with a group selected from F, CN, $OCH_3$, or $OCF_3$;

wherein $R_{13}$ is selected from H; $C_{1-10}$ alkyl optionally substituted with a group selected from F, CN, $OCH_3$, or $OCF_3$; $C_{3-7}$ cycloalkyl optionally substituted with a group selected from F, CN, $OCH_3$, or $OCF_3$; 4-7-membered heterocyclic group being saturated or unsaturated and having 1-3 hetero atoms and 3-6 carbon atoms optionally substituted with a group selected from F, CN, $OCH_3$, or $OCF_3$; $OC_{1-10}$alkyl optionally substituted with a group selected from F, CN, $OCH_3$, or $OCF_3$; $OC_{3-7}$cycloalkyl optionally substituted with a group selected from F, CN, $OCH_3$, or $OCF_3$; O-(4-7-membered heterocyclic group being saturated or unsaturated and having 1-3 hetero atoms and 3-6 carbon atoms) optionally substituted with a group selected from F, CN, $OCH_3$, or $OCF_3$; $NHC_{1-10}$ alkyl optionally substituted with a group selected from F, CN, $OCH_3$, or $OCF_3$; $NHC_{3-7}$cycloalkyl optionally substituted with a group selected from F, CN, $OCH_3$, or $OCF_3$; or NH-(4-7-membered heterocyclic group being saturated or unsaturated and having 1-3 hetero atoms and 3-6 carbon atoms) optionally substituted with a group selected from F, CN, $OCH_3$, or $OCF_3$;

wherein $R_{16}$ is selected from $C_{1-10}$ alkyl optionally substituted with a group selected from F, CN, $OCH_3$, or $OCF_3$; $C_{3-7}$ cycloalkyl optionally substituted with a group selected from F, CN, $OCH_3$, or $OCF_3$; or 4-7-membered heterocyclic group being saturated or unsaturated and having 1-3 hetero atoms and 3-6 carbon atoms optionally substituted with a group selected from F, CN, $OCH_3$, or $OCF_3$, wherein $R_{17}$ is selected from $C_{1-10}$ alkyl optionally substituted with a group selected from F, CN, $OCH_3$, or $OCF_3$; $C_{3-7}$ cycloalkyl optionally substituted with a group selected from F, CN, $OCH_3$, or $OCF_3$; or 4-7-membered heterocyclic group being saturated or unsaturated and having 1-3 hetero atoms and 3-6 carbon atoms optionally substituted with a group selected from F, CN, $OCH_3$, or $OCF_3$, or a pharmaceutically acceptable salt or solvate thereof.

In an embodiment $R_1$ is selected from H; Cl; Br; I; F; $CF_3$; $OCH_3$; $OCF_3$; $NH_2$, OH; CN; $NH_2$—$COCH_3$; $NH_2$—$COCF_3$. In a further embodiment $R_1$ is selected from H or F, such as H.

In a further embodiment $R_2$ is selected from H; Cl; Br; I; F; $CF_3$; $OCH_3$; $OCF_3$; $NH_2$, OH; CN; $NH_2$—$COCH_3$; $NH_2$—$COCF_3$. In a still further embodiment R2 is selected from H or F, such as F.

In a further embodiment $R_3$ is selected from H; Cl; Br; I; F; $CF_3$; $OCH_3$; $OCF_3$; $NH_2$, OH; CN; $NH_2$—$COCH_3$; $NH_2$—$COCF_3$. In a still further embodiment R3 is selected from H or F, such as F.

In a further embodiment $R_4$ is selected from H; Cl; Br; I; F; $CF_3$; $OCH_3$; $OCF_3$; $NH_2$, OH; CN; $NH_2$—$COCH_3$; $NH_2$—$COCF_3$. In a still further embodiment R4 is selected from H or F, such as F.

In a further embodiment $R_5$ is selected from H; Cl; Br; I; F; $CF_3$; $OCH_3$; $OCF_3$; $NH_2$, OH; CN; $NH_2$—$COCH_3$; $NH_2$—$COCF_3$. In a still further embodiment R5 is selected from H or F, such as H.

In a further embodiment $R_6$ is selected from $NH_2$; OH, CN, $C_{1-6}$ alkyl, optionally substituted with a group selected from F; $C_{3-7}$ cycloalkyl, optionally substituted with a $C_{1-4}$ alkyl optionally substituted with a F; branched $C_{3-10}$ alkyl, optionally substituted with a $C_{1-4}$ alkyl optionally substituted with a F; a 4-7-membered heterocyclic group being saturated or unsaturated and having 1-3 hetero atoms and 3-6 carbon atoms, optionally substituted with a $C_{1-4}$ alkyl optionally substituted with a F; Oxo; O—$C_{1-3}$ alkyl optionally substituted with a F.

In a still further embodiment $R_6$ is selected from $C_{1-6}$ alkyl, optionally substituted with a F; $C_{3-7}$ cycloalkyl, optionally substituted with a methyl optionally substituted with a F; branched $C_{3-6}$ alkyl, optionally substituted with a methyl optionally substituted with a F; a 4-7-membered heterocyclic group being saturated or unsaturated and having 1-3 hetero atoms and 3-6 carbon atoms, optionally substituted with a methyl optionally substituted with a F; Oxo; and $OCH_3$ optionally substituted with a F.

In a further embodiment $R_6$ is selected from branched $C_{3-6}$ alkyl, such as iso-propyl.

In a still further embodiment $R_6$ is selected from an 6-membered heterocyclic group being saturated and having 1-2 hetero atoms and 3-5 carbon atoms, optionally substituted with a $C_{1-4}$ alkyl.

In a further embodiment $R_6$ is selected from a piperidinyl, piperazinyl, morpholinyl, and tetrahydropyranyl, optionally substituted with a $C_{1-4}$ alkyl, such as methyl.

In a still further embodiment $R_9$ is selected from H; $NH_2$; OH, CN, $C_{1-6}$ alkyl, optionally substituted with a group selected from F; $C_{3-7}$ cycloalkyl, optionally substituted with a $C_{1-4}$ alkyl optionally substituted with a F; branched $C_{3-10}$ alkyl, optionally substituted with a $C_{1-4}$ alkyl optionally substituted with a F; a 4-7-membered heterocyclic group being saturated or unsaturated and having 1-3 hetero atoms and 3-6 carbon atoms, optionally substituted with a $C_{1-4}$ alkyl optionally substituted with a F; Oxo; O—$C_{1-3}$ alkyl optionally substituted with a F. In a further embodiment $R_9$ is H.

In a still further embodiment the compound of formula (1) is selected from
  3,3'-Dideoxy-3 -[4-(morpholin-4-yl)-1H-1,2,3-triazol- 1-yl]-3'-[4-(3,4,5-trifluorophenyl)-1H-1,2,3-triazol-1-yl]-1,1'-sulfanediyl-di-β-D-galactopyranoside,
  3,3'-Dideoxy-3-[4-(4-methylpiperazin-1-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside,
  3,3'-Dideoxy-3-[4-(piperidin-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside,
  3,3'-Dideoxy-3-[4-(tetrahydropyran-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside, and
  3,3'-Dideoxy-3-[4-(propan-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside.

In a further aspect the present invention relates to a compound of formula 1 of the present invention for use as a medicine.

In a still further aspect the present invention relates to a pharmaceutical composition comprising a compound of formula 1 of the present invention and optionally a pharmaceutically acceptable additive, such as carrier or excipient.

In a further aspect the present invention relates to a compound of formula 1 of the present invention for use in a method for treating a disorder relating to the binding of a galectin, such as galectin-1 and galectin-3 to a ligand in a mammal, such as a human.

In an embodiment the disorder is selected from the group consisting of inflammation; fibrosis, such as pulmonary fibrosis, liver fibrosis, kidney fibrosis, ophtalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization. In another embodiment the disorder is selected from proliferative vitreoretinopathy.

In a still further aspect the present invention relates to a method for treatment of a disorder relating to the binding of a galectin, such as galectin-1 and galectin-3, to a ligand in a mammal, such as a human, wherein a therapeutically effective amount of at least one compound of formula 1 of the present invention is administered to a mammal in need of said treatment.

In an embodiment the disorder is selected from the group consisting of inflammation; fibrosis, such as pulmonary fibrosis, liver fibrosis, kidney fibrosis, ophtalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization. A non-limiting group of cancers given as examples of cancers that may be treated, managed and/or prevented by administration of a compound of formula (1) include: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer. Each of these disorders is considered a single embodiment and may be made the subject of a claim specifically to such disease or disorder.

Another aspect of the present invention concerns combination therapy involving administering a compound of formula (1) of the present invention together with a therapeutically active compound different from the compound of formula (1) (interchangeable with "a different therapeutically active compound"). In one embodiment the present invention relates to a combination of a compound of formula (1) and a different therapeutically active compound for use in treatment of a disorder relating to the binding of a galectin-3, to a ligand in a mammal. Such disorders are disclosed below.

In an embodiment of the present invention, a therapeutically effective amount of at least one compound of formula (1) of the present invention is administered to a mammal in need thereof in combination with a different therapeutically active compound. In a further embodiment, said combination of a compound of formula (1), in combination with a different therapeutically active compound is administered to a mammal suffering from a disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis.

A non-limiting group of cancers given as examples of cancers that may be treated, managed and/or prevented by administration of a compound of formula (1) in combination with a different therapeutically active compound is selected from: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute non-lymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hairy cell leukemia and thyroid cancer.

In some aspects of the present invention, the administration of at least one compound of formula (1) of the present invention and at least one additional therapeutic agent demonstrate therapeutic synergy. In some aspects of the methods of the present invention, a measurement of response to treatment observed after administering both at least one compound of formula (1) of the present invention and the additional therapeutic agent is improved over the same measurement of response to treatment observed after administering either the at least one compound of formula (1) of the present invention or the additional therapeutic agent alone.

A further aspect of the present invention concerns combination therapy involving administering a compound of formula (1) of the present invention together with an anti-fibrotic compound different form the compound of formula (1) to a mammal in need thereof. In a further embodiment, such anti-fibrotic compound may be selected from the following non-limiting group of anti-fibrotic compounds: pirfenidone, nintedanib, simtuzumab (GS-6624, AB0024), BG00011 (STX100), PRM-151, PRM-167, PEG-FGF21, BMS-986020, FG-3019, MN-001, IW001, SAR156597, GSK2126458, and PBI-4050.

A still further aspect of the present invention concerns combination therapy involving administering a compound of formula (1) in combination with a further conventional cancer treatment such as chemotherapy or radiotherapy, or treatment with immunostimulating substances, gene therapy, treatment with antibodies and treatment using dendritic cells, to a mammal in need thereof.

In an embodiment the compound of formula (1) is administered together with at least one additional therapeutic agent selected from an antineoplastic chemotherapy agent. In a further embodiment, the antineoplastic chemotherapeutic agent is selected from: alltrans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

In a further embodiment of the present invention, the further conventional cancer treatment includes radiation therapy. In some embodiments, radiation therapy includes localized radiation therapy delivered to the tumor. In some embodiments, radiation therapy includes total body irradiation.

In other embodiments of the present invention the further cancer treatment is selected from the group of immunostimulating substances e.g. cytokines and antibodies. Such as cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance: c-Cbl, Cbl-b, GRAIL, Itch and Nedd4 each negatively regulate T cell growth factor production and proliferation.

In some embodiments of the present invention the compound of formula (1) is administered together with at least one additional therapeutic agent selected from a checkpoint inhibitor. In some embodiments of the invention, the checkpoint inhibitor is acting on one or more of the following, non-limiting group of targets: CEACAM1, galectin-9, TIM3, CD80, CTLA4, PD-1, PD-L1, HVEM, BTLA, CD160, VISTA, B7-H4, B7-2, CD155, CD226, TIGIT, CD96, LAG3, GITF, OX40, CD137, CD40, IDO, and TDO. These are know targets and some of these targets are described in Melero et al., Nature Reviews Cancer (2015).

In some embodiments of the present invention the compound of formula (1) is administered together with at least one additional therapeutic agent selected from an inhibitor of indoleamine-2,3-dioxygenase (IDO).

In some embodiments of the present invention the compound of formula (1) is administered together with at least one additional therapeutic agent selected from one or more inhibitors of the CTLA4 pathway. In some embodiments, the inhibitor of the CTLA4 pathway is selected from one or more antibodies against CTLA4.

In some embodiments of the present invention the compound of formula (1) is administered together with at least one additional therapeutic agent selected from one or more inhibitors of the PD-1/PD-L pathway. In some embodiments, the one or more inhibitors of the PD-1/PD-L pathway are selected from one or more antibodies against PD-1, PD-L1, and/or PD-L2.

In a further aspect the present invention relates to a method for treatment of a disorder relating to the binding of a galectin, such as galectin-3, to a ligand in a mammal, such as a human, wherein a therapeutically effective amount of at least one compound according to any one of the claims 1-11 is administered to a mammal in need of said treatment. In an embodiment the disorder is selected from the group consisting of inflammation; fibrosis, such as pulmonary fibrosis, liver fibrosis, kidney fibrosis, ophtalmological fibrosis and fibrosis of the heart; septic shock; cancer; autoimmune diseases; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization. In a further embodiment the disorder is selected from proliferative vitreoretinopathy.

In a still further aspect the present invention relates to a process of preparing a compound of formula 1 or a pharmaceutically acceptable salt or solvate thereof comprising the steps a1:

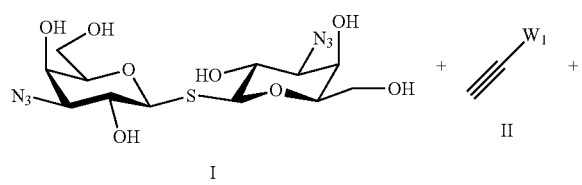

I

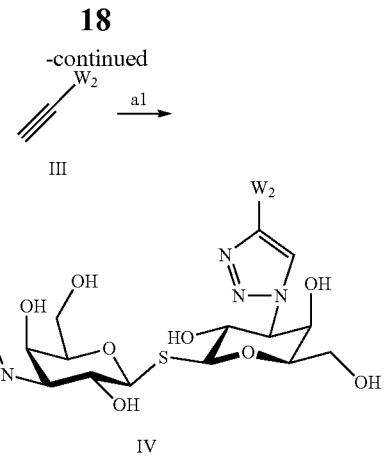

IV a1) Reacting the compound of formula I (which may be obtained as described in WO2009139719) with a compound of formula II, wherein $W_1$ is a phenyl optionally substituted with $R_1$-$R_5$ as defined in formula 1, in an inert solvent, such as DMF, using a base, such as diisopropylamine, catalyzed by CuI. The product of such a reaction is then reacted further with III, wherein $W_2$ is defined as $R_6$ in formula 1, in an inert solvent, such as DMF, using a base, such as diisopropylamine, catalyzed by CuI to give compounds of formula IV. An alternative approach would be to react a compound of formula I with a compound of formula III followed by a compound of formula II using similar conditions described above.

In a still further aspect the present invention relates to a process of preparing a compound of formula 1 or a pharmaceutically acceptable salt or solvate thereof comprising the step a2:

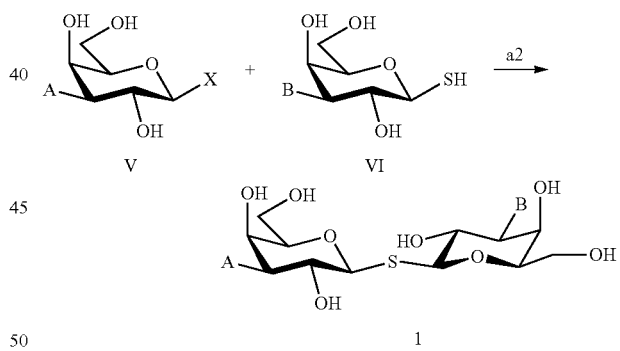

a2) reacting the compound of formula V with a compound of formula VI. The sulfur of VI could be unsubstituted or protected as a thiourea, a silyl protective groups, such as Triisopropylsilane (TIPS) or other protective group. When protected as thiourea the coupling could be performed using a weak organic base such as triethylamine. When protected using a silyl protective group in the presence of a reagent, such as tetrabutylammoniumfluoride, the product is then further treated with a base such as sodium methoxide to remove acetate protective groups to provide the compound of formula 1.

In a still further aspect the present invention relates to a process of preparing a compound of formula 1 or a pharmaceutically acceptable salt or solvate thereof comprising the step a3:

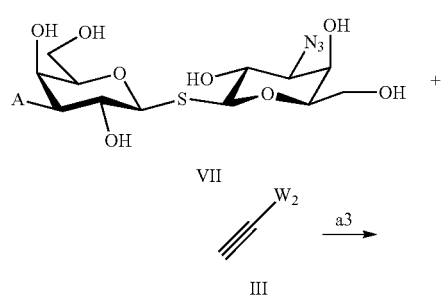

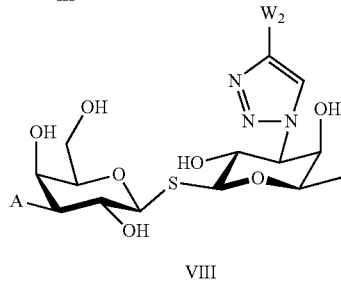

a3)
reacting the compound of formula VII with a compound of formula III in an inert solvent, such as DMF, using a base, such as diisopropylamine, catalyzed by CuI to give compounds of formula VIII.

In a still further aspect the present invention relates to a process of preparing a compound of formula XI, XII and XIII comprising the steps a4-a6:

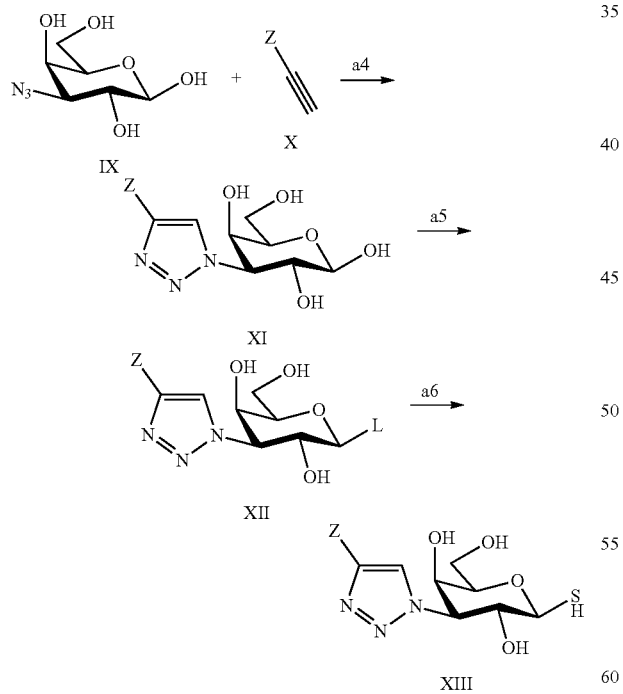

a4) reacting a compound of formula IX with a compound of formula X wherein Z is defined as either W1 or W2, in an inert solvent, such as DMF, using a base, such as diisopropylamine, catalyzed by CuI would provide a compound of formula XI.

a5) Reacting the compound of the formula XI with TiBr$_4$, washing with aqueous NaHCO$_3$ in order to give a compound of the formula XII wherein L is a leaving group, such as Br;

a6) Reacting a compound of the formula XII with triisopropylsilanethiol in an inert solvent, such as acetone, to provide the compound of formula XIII wherein the sulfur is protected with triisopropylsilane; optionally the compound of formula XII could be reacted with thiourea in an inert solvent, such as acetonitrile, optionally at elevated temperatures to give a compound of formula XIII.

In a still further aspect the present invention relates to a process of preparing a compound of formula XIV and XV comprising the steps a7-a8:

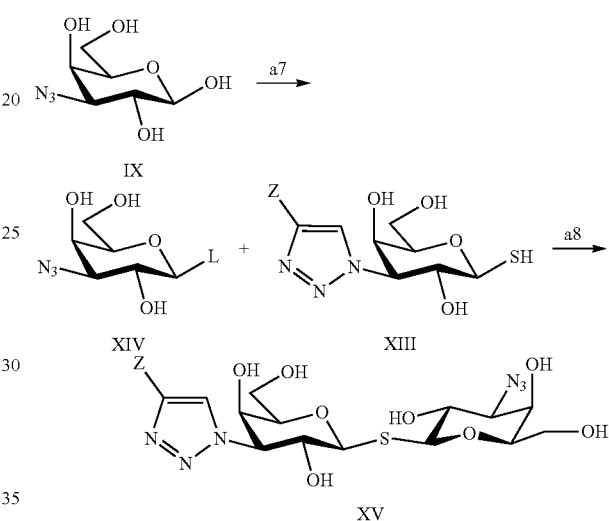

a7) Reacting the compound of the formula IX with TiBr$_4$, washing with aqueous NaHCO$_3$ in order to give a compound of the formula XIV wherein L is a leaving group, such as Br;

a8) reacting the compound of formula XIV with a compound of formula XIII The sulfur of XIII could be unsubstituted or protected as a thiourea, a silyl protective group, such as Triisopropylsilane (TIPS) or other protective group. When protected as thiourea the coupling could be performed using an organic base such as triethylamine When protected using a silyl protective group in the presence of a reagent, such as tetrabutylammoniumfluoride to give a compound of formula XV.

In a still further aspect the present invention relates to a process of preparing a compound of formula X comprising the step a9:

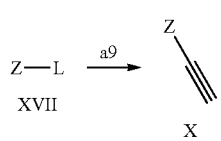

a9) Reacting a compound of formula XVII wherein Z is defined as W$_1$ and L is defined as a leaving group such as bromine, with trimethylsilane-acetylene using a palladium catalyst such as bis(triphenylphosphine)palladium-(II)-chloride and a base like diisopropylamine in an inert solvent, such as THF, to give a compound of formula X.

In a still further aspect the present invention relates to a process of preparing a compound of formula X comprising the step a10:

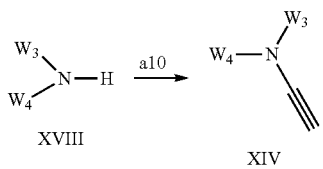

a10) Reacting a compound of formula XVIII with a base such as BuLi in an inert solvent such as THF, followed by reaction with with a reagent such as trichloroethylene. The product of this reaction is further reacted with a base such as BuLi followed by reaction with trimethylsilyl chloride, to give a compound of formula XIV.

The skilled person will understand that it may be necessary to adjust or change the order of steps in the processes a1 to a10, and such change of order is encompassed by the aspects of the process as described above in the reaction schemes and accompanying description of the process steps.

Furthermore the skilled person will understand that the processes described above and hereinafter the functional groups of intermediate compounds may need to be protected by protecting group.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g., t-butyldimethylsilyl, t-butyldipheylsilyl or trimethylsilyl), AcO (acetoxy), TBS(t-butyldimethylsilyl), TMS(trimethylsilyl), PMB (p-methoxybensyl), and tetrahydropyranyl. Suitable protecting groups for carboxylic acid include (C1-C6)-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include S—C(=N)NH$_2$, TIPS.

The protection and deprotection of functional groups may take place before or after any reaction in the above mentioned processes.

Furthermore the skilled person will appreciate that, in order to obtain compounds of the invention in an alternative, and on some occasions, more convenient, manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

In a still further embodiment the compound of formula 1 is on free form. In one embodiment the free form is an anhydrate. In another embodiment the free form is a solvate, such as a hydrate.

In a further embodiment the compound is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

Alternative Formulations

Two small molecule galectin-3 inhibitors, 3,3'-Dideoxy-3,3'-bis-[4-(3-fluoro-phenyl)-1H-1,2,3-triazol-1-yl]-1,1'-sulfanediyl-di-β-D-galactopyranoside (GB1A) and 3,3'-Dideoxy-3,3'-bis-[4-(5-fluoro-2-pyridinyl)-1H-1,2,3-triazol-1-yl]-1,1'-sulfanediyl-di-β-D-galactopyranoside (GB1B) were tested in an efficacy study of the anti-fibrotic potential in a rabbit model of proliferative Vitreoretinopathy (PVR) in liquid compositions containing HEC. It has been demonstrated that the use of HEC provided a markedly reduction in corneal angiogenesis and fibrosis compared to PBS and/or DMSO. The two galectin-3 inhibitors were highly effective at reducing the size and number of subretinal glial scars as well as the number of dividing cells, providing a potential new therapeutic strategy for treating ocular disorders related to pathological angiogenesis and fibrosis, in particular PVR in mammals, such as humans.

In a further aspect, the present invention also relates to a composition comprising hydroxyethyl cellulose (HEC) and a drug for treatment of an eye disease, disorder or condition. In an embodiment the composition is for use in a method for treatment of ocular angiogenesis or ocular fibrosis, such as for treatment of proliferative vitreoretinopathy. In a further embodiment the drug is a galectin inhibitor, such as a galectin-3 inhibitor. In a further embodiment the drug is selected from a structure comprising an α-D-galactopyranose, a β-D-galactopyranose, a C3-[1,2,3]-triazol-1-yl-substituted α-D-galactopyranose, a C3-[1,2,3]-triazol-1-yl-substituted β-D-galactopyranose, a thio-digalectoside, or a C3-[1,2,3]-triazol-1-yl-substituted thio-digalectoside. In a further embodiment, the drug is present in a therapeutically effective amount. In a further embodiment, the drug is selected from any one of the structures and embodiments disclosed in U.S. Ser. No. 10/466,933. In a further embodiment, the drug is selected from any one of the structures and embodiments disclosed in U.S. Ser. No. 11/561,124. In a further embodiment, the drug is selected from any one of the structures and embodiments disclosed in U.S. Ser. No. 11/561,465. In a further embodiment, the drug is selected from any one of the structures and embodiments disclosed in U.S. Ser. No. 12/992,328. In a further embodiment, the drug is selected from any one of the structures and embodiments disclosed in U.S. Ser. No. 13/266,960. In a further embodiment, the drug is selected from any one of the structures and embodiments disclosed in U.S. Ser. No. 14/364,169. In a further embodiment, the drug is selected from any one of the structures and embodiments disclosed in PCT/EP2015/065313. In a further embodiment, the drug is selected from any one of the structures and embodiments disclosed in PCT/EP2016/050633. In a further embodiment, the drug is selected from any one of the structures and embodiments disclosed in PCT/EP2016/051836. In a further embodiment, the drug is selected from any one of the structures and embodiments disclosed in claims 1-15 herein.

In a still further aspect the present invention also relates to a composition comprising hydroxyethyl cellulose (HEC) and a galectin inhibitor for use in a method for treatment of ocular angiogenesis or ocular fibrosis, such as for treatment of proliferative vitreoretinopathy. In an embodiment the composition comprises hydroxyethyl cellulose (HEC) and a galectin inhibitor for use in a method for treatment of proliferative vitreoretinopathy. In a further embodiment the galectin inhibitor is selected from a galectin-3 inhibitor. In a further embodiment the galectin inhibitor, such as galectin-3 inhibitor, is present in a therapeutically effective amount. In a further embodiment the galectin inhibitor, such as galectin-3 inhibitor, is selected from any one of the structures and embodiments disclosed in U.S. Ser. No. 10/466,933. In a further embodiment the galectin inhibitor, such as galectin-3 inhibitor, is selected from any one of the structures and embodiments disclosed in U.S. Ser. No. 11/561,124. In a further embodiment the galectin inhibitor, such as galectin-3 inhibitor, is selected from any one of the structures and embodiments disclosed in U.S. Ser. No. 11/561,465. In a further embodiment the galectin inhibitor, such as galectin-3 inhibitor, is selected from any one of the structures and embodiments disclosed in U.S. Ser. No. 12/992,328. In a further embodiment the galectin inhibitor, such as galectin-3 inhibitor, is selected from any one of the structures and embodiments disclosed in U.S. Ser. No. 13/266,960. In a further embodiment the galectin inhibitor, such as galectin-3 inhibitor, is selected from any one of the structures and embodiments disclosed in U.S. Ser. No. 14/364,169. In a further embodiment the galectin inhibitor, such as galectin-3 inhibitor, is selected from any one of the structures and embodiments disclosed in PCT/EP2015/065313. In a further embodiment the galectin inhibitor, such as galectin-3 inhibitor, is selected from any one of the structures and embodiments disclosed in PCT/EP2016/050633. In a further embodiment the galectin inhibitor, such as galectin-3 inhibitor, is selected from any one of the structures and embodiments disclosed in PCT/EP2016/051836. In a further embodiment the galectin inhibitor, such as galectin-3 inhibitor, is selected from any one of the structures and embodiments disclosed in claims 1-15 herein.

In a still further aspect the present invention also relates to a galectin inhibitor for use in a method for treatment of proliferative vitreoretinopathy. In a further embodiment the galectin inhibitor is selected from a galectin-3 inhibitor. In a further embodiment the galectin inhibitor, such as galectin-3 inhibitor, is present in a therapeutically effective amount. In a further embodiment the galectin inhibitor, such as galectin-3 inhibitor, is selected from any one of the structures and embodiments disclosed in U.S. Ser. No. 10/466,933. In a further embodiment the galectin inhibitor, such as galectin-3 inhibitor, is selected from any one of the structures and embodiments disclosed in U.S. Ser. No. 11/561,124. In a further embodiment the galectin inhibitor, such as galectin-3 inhibitor, is selected from any one of the structures and embodiments disclosed in U.S. Ser. No. 11/561,465. In a further embodiment the galectin inhibitor, such as galectin-3 inhibitor, is selected from any one of the structures and embodiments disclosed in U.S. Ser. No. 12/992,328. In a further embodiment the galectin inhibitor, such as galectin-3 inhibitor, is selected from any one of the structures and embodiments disclosed in U.S. Ser. No. 13/266,960. In a further embodiment the galectin inhibitor, such as galectin-3 inhibitor, is selected from any one of the structures and embodiments disclosed in U.S. Ser. No. 14/364,169. In a further embodiment the galectin inhibitor, such as galectin-3 inhibitor, is selected from any one of the structures and embodiments disclosed in PCT/EP2015/065313. In a further embodiment the galectin inhibitor, such as galectin-3 inhibitor, is selected from any one of the structures and embodiments disclosed in PCT/EP2016/050633. In a further embodiment the galectin inhibitor, such as galectin-3 inhibitor, is selected from any one of the structures and embodiments disclosed in PCT/EP2016/051836. In a further embodiment the galectin inhibitor, such as galectin-3 inhibitor, is selected from any one of the structures and embodiments disclosed in claims 1-15 herein.

In a still further aspect the present invention also relates to an aqueous composition comprising HEC and a galectin inhibitor. In an embodiment the aqueous composition is for use in a method for treatment of ocular angiogenesis or ocular fibrosis, such as for treatment of proliferative vitreoretinopathy. In a further embodiment the galectin inhibitor is selected from a galectin-3 inhibitor. In a further embodiment the galectin inhibitor, such as galectin-3 inhibitor, is present in a therapeutically effective amount. In a further embodiment the galectin inhibitor, such as galectin-3 inhibitor, is selected from any one of the structures and embodiments disclosed in U.S. Ser. No. 10/466,933. In a further embodiment the galectin inhibitor, such as galectin-3 inhibitor, is selected from any one of the structures and embodiments disclosed in U.S. Ser. No. 11/561,124. In a further embodiment the galectin inhibitor, such as galectin-3 inhibitor, is selected from any one of the structures and embodiments disclosed in U.S. Ser. No. 11/561,465. In a further embodiment the galectin inhibitor, such as galectin-3 inhibitor, is selected from any one of the structures and embodiments disclosed in U.S. Ser. No. 12/992,328. In a further embodiment the galectin inhibitor, such as galectin-3 inhibitor, is selected from any one of the structures and embodiments disclosed in U.S. Ser. No. 13/266,960. In a further embodiment the galectin inhibitor, such as galectin-3 inhibitor, is selected from any one of the structures and embodiments disclosed in U.S. Ser. No. 14/364,169. In a further embodiment the galectin inhibitor, such as galectin-3 inhibitor, is selected from any one of the structures and embodiments disclosed in PCT/EP2015/065313. In a further embodiment the galectin inhibitor, such as galectin-3 inhibitor, is selected from any one of the structures and embodiments disclosed in PCT/EP2016/050633. In a further embodiment the galectin inhibitor, such as galectin-3 inhibitor, is selected from any one of the structures and embodiments disclosed in PCT/EP2016/051836. In a further embodiment the galectin inhibitor, such as galectin-3 inhibitor, is selected from any one of the structures and embodiments disclosed in claims 1-15 herein. Such aqueous composition may be suitable for topical or injection administration to an eye of a mammal. Thus, in a further embodiment the aqueous composition is selected from a suspension or solution of eye drops for topical administration to the eye of a mammal. In another embodiment the aqueous composition is selected from a suspension or solution for injection administration to the eye of a mammal. The suspension or solution of eye drops may in a further embodiment be a gel.

In a still further aspect the present invention relates to a method for treatment of ocular angiogenesis or ocular fibrosis, such as for treatment of proliferative vitreoretinopathy, in a mammal, such as a human, wherein a composition comprising hydroxyethyl cellulose (HEC) and a therapeutically effective amount of a galectin inhibitor, such as a galectin-3 inhibitor, is administered to a mammal in need of said treatment. In an embodiment the composition is an aqueous composition, such as a solution or suspension. In a further embodiment the galectin inhibitor, such as galectin-3 inhibitor, is selected from any one of the structures and embodiments disclosed in U.S. Ser. No. 10/466,933. In a further embodiment the galectin inhibitor, such as galectin-3 inhibitor, is selected from any one of the structures and embodiments disclosed in U.S. Ser. No. 11/561,124. In a further embodiment the galectin inhibitor, such as galectin-3 inhibitor, is selected from any one of the structures and embodiments disclosed in U.S. Ser. No. 11/561,465. In a further embodiment the galectin inhibitor, such as galectin-3 inhibitor, is selected from any one of the structures and embodiments disclosed in U.S. Ser. No. 12/992,328. In a further embodiment the galectin inhibitor, such as galectin-3 inhibitor, is selected from any one of the structures and embodiments disclosed in U.S. Ser. No. 13/266,960. In a further embodiment the galectin inhibitor, such as galectin-3 inhibitor, is selected from any one of the structures and embodiments disclosed in U.S. Ser. No. 14/364,169. In a further embodiment the galectin inhibitor, such as galectin-3 inhibitor, is selected from any one of the structures and embodiments disclosed in PCT/EP2015/065313. In a further embodiment the galectin inhibitor, such as galectin-3 inhibitor, is selected from any one of the structures and embodiments disclosed in PCT/EP2016/050633. In a further embodiment the galectin inhibitor, such as galectin-3 inhibitor, is selected from any one of the structures and embodiments disclosed in PCT/EP2016/051836. In a further embodiment the galectin inhibitor, such as galectin-3 inhibitor, is selected from any one of the structures and embodiments disclosed in claims 1-15 herein.

When a galectin inhibitor, such as a galectin-3 inhibitor, is used in the above aspects and embodiments, it is suitably present in a therapeutically effective amount that provides the most optimal conditions for the eye to be treated. Thus, in an embodiment the galectin inhibitor, such as the galectin-3 inhibitor, is present in an amount from 0.01 mg/ml to 100 mg/ml, more preferred 0.05 mg/ml to 50 mg/ml, even more preferred 0.1 mg/ml to 20 mg/ml, typically 0.5 mg/ml to 10 mg/ml.

When HEC is used in the above aspects and embodiments, it is suitably present in an amount that provides the most optimal conditions for the eye to be treated. Thus, in an embodiment HEC is present in an amount from 0.1 weight % to 5 weight %, more preferred 0.25 weight % to 4 weight %, even more preferred 0.5 weight % to 3 weight %, typically 0.5 weight % to 2 weight %.

Definitions

The term "$C_{1-10}$ alkyl" as used herein means an alkyl group containing 1-10 carbon atoms, e.g. $C_{1-5}$ or $C_{1-6}$, such as methyl, ethyl, propyl, butyl, pentyl or hexyl.

The term "branched $C_{3-10}$ alkyl" as used herein means a branched alkyl group containing 3-10 carbon atoms, such as 3-6 carbon atoms, e.g. isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl.

The term "a 4-7 membered heterocyclic group being saturated or unsaturated and having 1-3 hetero atoms and 3-6 carbon atoms" as used herein means a cyclic group having 1-3 N, S, or O atoms and optionally containing 1, 2 or 3 double bonds in the ring, such as piperazinyl, piperidinyl, morpholinyl, tetrahydropyranyl, tetrahydrothiophenyl, tetrahydrofuranyl, pyrrolidinyl, imidazolidinyl, pyrazolidinyl, isothiazolidinyl, isooxazolidinyl, thiazolidinyl, oxazolidinyl, hexahydropyrimidinyl, pyridazinyl, azepanyl, oxepanyl, dioxepanyl, diazepanyl, or oxazepanyl.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "Oxo" as used herein means an oxygen atom with double bonds, also indicated as =O.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular, a human being, but it may also include animals, such as dogs, cats, cows, sheep and pigs.

The term "a therapeutically effective amount" of a compound of formula (1) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (1) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compound as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, suspensions, lyophilized powders, gels, creams, lotions, ointments, pastes, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental Procedures

Evaluation of Kd Values

The affinity of Example 1-5 for galectins were determined by a fluorescence anisotropy assay where the compound was used as an inhibitor of the interaction between galectin and a fluorescein tagged saccharide probe as described Sörme, P., Kahl-Knutsson, B., Huflejt, M., Nilsson, U. J., and Leffler H. (2004) Fluorescence polarization as an analytical tool to evaluate galectin-ligand interactions. Anal. Biochem. 334: 36-47, (Sörme et al., 2004) and Monovalent interactions of Galectin-1 By Salomonsson, Emma; Larumbe, Amaia; Tejler, Johan; Tullberg, Erik; Rydberg, Hanna; Sundin, Anders; Khabut, Areej; Frejd, Torbjorn; Lobsanov, Yuri D.; Rini, James M.; et al, From Biochemistry (2010), 49(44), 9518-9532, (Salomonsson et al., 2010). The assay was also adapted to be able to measure the high affinity of compounds for galectin-3 by using the below probe constructed to have high affinity for galectin-3 which made it possible to use a low concentration of galectin-3 (10 nM). 100 nM albumin was included as a carrier to prevent protein loss at such low concentration of galectin.

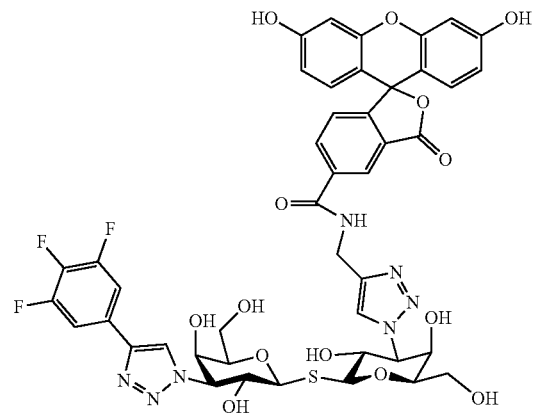

Probe

| Ex. | Name | Structure | Gal-3 Kd (μM) | Gal-1 Kd (μM) | Solubility (mg/mL) |
|---|---|---|---|---|---|
| 1 | 3,3'-Dideoxy-3-[4-(morpholin-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside | 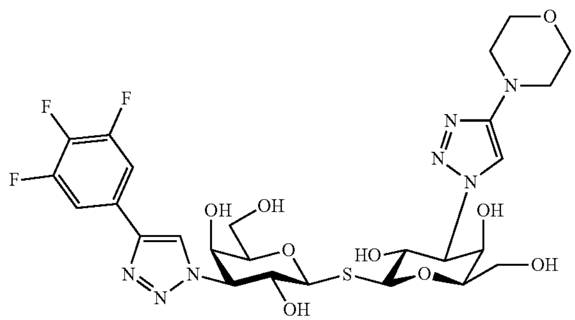 | 0.002 | 0.110 | >10 |
| 2 | 3,3'-Dideoxy-3-[4-(4-methylpiperazin-1-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside | 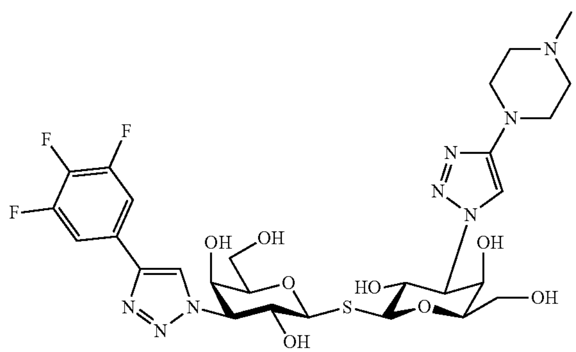 | 0.007 | 0.035 | >10 |
| 3 | 3,3'-Dideoxy-3-[4-(piperidin-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside | 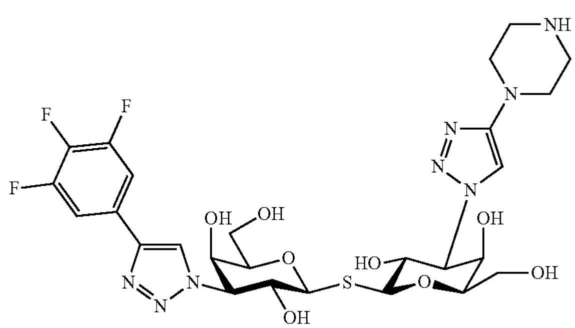 | 0.005 | 0.029 | >10 |
| 4 | 3,3'-Dideoxy-3-[4-(tetrahydropyran-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside | 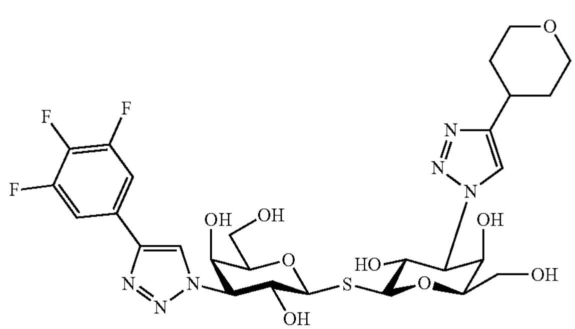 | 0.001 | 0.058 | 8.1 |

-continued

| Ex. | Name | Structure | Gal-3 Kd (µM) | Gal-1 Kd (µM) | Solubility (mg/mL) |
|-----|------|-----------|---------------|---------------|--------------------|
| 5 | 3,3'-Dideoxy-3-[4-(propan-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside | 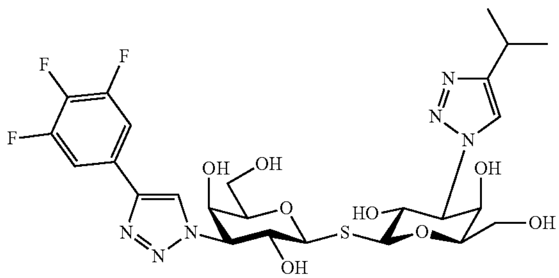 | 0.002 | 0.070 | >10 |

Ex. = Example  Gal = Galectin

General Procedures

Nuclear Magnetic Resonance (NMR) spectra were recorded on a 400 MHz Varian or a 500 MHz Bruker AVANCE III 500 instrument, at 25° C. Chemical shifts are reported in ppm (δ) using the residual solvent as internal standard. Peak multiplicities are expressed as follow: s, singlet; d, doublet; dd, doublet of doublets; t, triplet; dt, doublet of triplet; q, quartet; m, multiplet; br s, broad singlet.

LC-MS were acquired on an Agilent 1100 or Agilent 1200 HPLC coupled with an Agilent MSD mass spectrometer operating in ES (+) ionization mode. Columns: Waters symmetry 2.1×30 mm C18, Chromolith RP-18 2×50 mm or XBridge C18 (4.6×50 mm, 3.5 µm) or SunFire C18 (4.6×50 mm, 3.5 µm). Solvent A water+0.1% TFA and solvent B Acetonitrile+0.1% TFA. Wavelength: 254 nM Preparative HPLC was performed on a Gilson system. A) Flow: 10 ml/min Column: kromasil 100-5-C18 column Wavelength: 254 nM. Solvent A water+0.1% TFA and solvent B Acetonitrile+0.1% TFA. B) on a Gilson 215. Flow: 25 ml/min Column: XBrige prep C18 10 µm OBD (19×250 mm) column Wavelength: 254 nM. Solvent A water (10 mM Ammonium hydrogen carbonate) and solvent B Acetonitrile. Flash chromatography was perfomed on a Biotage SP1 automated system, using Biotage Snap KP-Sil 25 g or 50 g cartridges.

SYNTHESIS OF EXAMPLES 1-5

Example 1

3,3'-Dideoxy-3-[4-(morpholin-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside

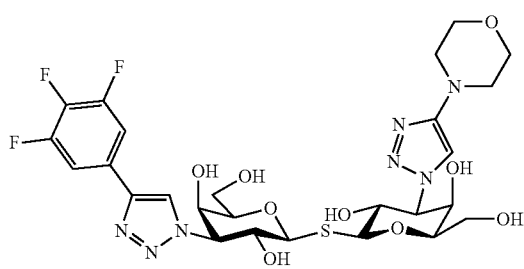

4-[2-(Trimethylsilyethynyl)-morpholine (117 µL) was dissolved in MeCN (5 mL, dry) and triethylamine trihydrofluoride (36 µL) was added and the mixture was stirred at r.t. under Na. After 1 h the mixture was added to i2 (121 mg) dissolved in MeCN (5 mL) and cop-per(I) iodide (40 mg) was added followed by Hünig's base (78 µL). After 18 h the temperature was increased to 40° C. and after another 24 h the temperature was increased to 50° C. and copper(I) iodide (40 mg) was added. After another four hours 4-[2-(trimethylsilyl)ethynyl]-morpholine (100 µL), TBAF (161 mg), and Hünig's base (80 µL) was added. After 18 h the mixture was concentrated down and purified by flash chromatography ($SiO_2$/Petroleum ether:EtOAc 100:0→0:100). The residue was dissolved in MeOH (20 mL, dry) and NaOMe (1M in MeOH, 1.0 mL) was added and the mixture was stirred at r.t. After 2 h HOAc (2 mL) was added and the mixture was concentrated down. The residue was purified by HPLC ($C_{18}$/MeCN:$H_2O$:0.1% TFA). Freezedrying afforded the title compound as a white solid (107 mg). $^1$H NMR (400 MHz, Methanol-$d_4$) δ 8.57 (s, 1H), 7.64 (s, 1H), 7.64-7.56 (m, 2H), 4.93-4.72 (m, 4H), 4.74-4.68 (m, 2H), 4.12 (bs, 2H), 3.89-3.76 (m, 8H), 3.74-3.65 (m, 2H), 3.18-3.10 (m, 4H). ESI-MS m/z calcd for $[C_{26}H_{33}F_3N_7O_9S]^+$ (M+H)$^+$: 676.19; found: 676.20.

Example 2

3,3'-Dideoxy-3-[4-(4-methylpiperazin-1-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside

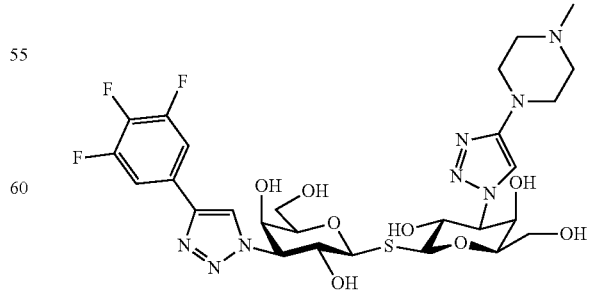

Methylpiperazine (8.5 mL) was dissolved in THF (30 mL) and cooled to −60° C. n-BuLi (48 mL, 1.6M in hexanes) was added. The mixture was allowed to warm to r.t. and then stirred 1 h. This mixture was added, via a dropping funnel, to a solution of trichloroethylene (6.85 mL) in THF (30 mL) at −50° C. The resulting mixture was allowed to adopt r.t. and then stirred 1 h. It was again cooled and n-BuLi (100 mL, 1.6M in hexanes) was added keeping the temperature below −50° C. The mixture was left to slowly adopt r.t. and stirred overnight. The mixture was cooled to −60° C. and trimethylsilyl chloride (10 mL) was added dropwise. The mixture was allowed to reach r.t. and then stirred 3 h. It was filtered through a plug of celite and then concentrated in vacuo. The brown liquid residue was vacuum distilled. Trimethyl-[2-(4-methylpiperazin-1-yl)ethynyl]silane (6.30 g) was collected as a clear oil, boiling 50-65° C. $^1$H NMR (400 MHz, Chloroform-d) δ 3.09-3.01 (m, 4H), 2.40-2.29 (m, 4H), 2.23 (s, 3H), 0.08 (s, 9H).

Trimethyl-[2-(4-methylpiperazin-1-yl)ethynyl]silane (100 μL) was dissolved in MeCN (2 mL) while bubbling nitrogen through. Cesium fluoride (75 mg) was added. After 2 min, i2 (40 mg) in acetonitrile (5 mL) and copper(I) iodide (6 mg) were added and the mixture stirred 5 min. Hünig's base (200 μL) was added, the vial closed and stirred at r.t. for 4 h. The mixture was concentrated and the residue purified by flash chromatography (SiO$_2$/EtOAc:MeOH 100:0→80:20). This afforded a pale yellow oil 48 mg. This was dissolved in MeOH (15 mL) and NaOMe (1M in MeOH, 1 mL) was added and the mixture stirred for 2 h. TFA (0.2 mL) was added and the mixture concentrated in vacuo. The residue was purified by HPLC (C$_{18}$/MeCN:H$_2$O:0.1% TFA). Freezedrying afforded the product as a white powder (25 mg). $^1$H NMR (400 MHz, Methanol-d4) δ 8.55 (s, 1H), 7.70 (s, 1H), 7.61 (dd, J=8.5, 6.6 Hz, 2H), 4.89 (t, J=8.9 Hz, 2H), 4.77-4.54 (m, 4H), 4.13 (dd, J=11.5, 2.8 Hz, 2H), 3.91-3.76 (m, 4H), 3.75-3.66 (m, 2H), 3.44 (s, 4H), 3.33 (d, J=8.9 Hz, 4H), 2.89 (s, 3H). ESI-MS m/z calcd for [C$_{27}$H$_{36}$F$_3$N$_8$O$_8$S]$^+$ (M+H)$^+$: 689.23; found: 689.25.

Example 3

3,3'-Dideoxy-3-[4-(piperidin-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside

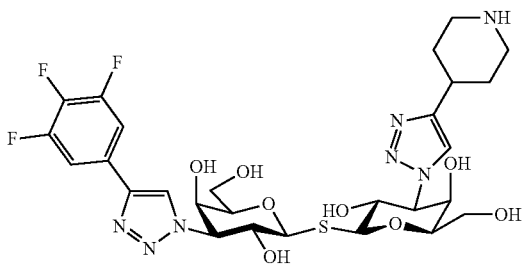

i1 (40 mg) and tert-butyl 4-ethynylpiperidine-1-carboxylate (35 mg) were dissolved in acetonitrile (4 mL) and degassed (argon). Copper(I) iodide (4 mg) was added followed by Hünig's base (100 μL). The mixture was stirred at r.t. overnight and then concentrated in vacuo. The residue was dissolved in CH$_2$Cl$_2$ (10 mL). TFA (1 mL) was added and the mixture stirred at 30° C. for 3 h. The mixture was concentrated in vacuo and the residue purified by HPLC (C$_{18}$/MeCN:H$_2$O:0.1% TFA). Freezedrying afforded a white fluffy solid (43 mg). $^1$H NMR (400 MHz, Methanol-d4) δ 8.55 (s, 1H), 8.03 (s, 1H), 7.66-7.57 (m, 2H), 4.95-4.79 (m, 2H), 4.67-4.52 (m, 2H), 4.13 (dd, J=14.0, 2.8 Hz, 2H), 3.91-3.76 (m, 4H), 3.70 (dd, J=11.2, 4.4 Hz, 2H), 3.47 (d, J=13.0 Hz, 2H), 3.15 (t, J=12.1 Hz, 3H), 2.26 (d, J=14.6 Hz, 4H), 1.94 (q, J=12.9 Hz, 4H). ESI-MS m/z calcd for [C$_{27}$H$_{35}$F$_3$N$_7$O$_8$S]$^+$ (M+H)$^+$: 674.21; found: 674.25.

Example 4

3,3'-Dideoxy-3-[4-(tetrahydropyran-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside

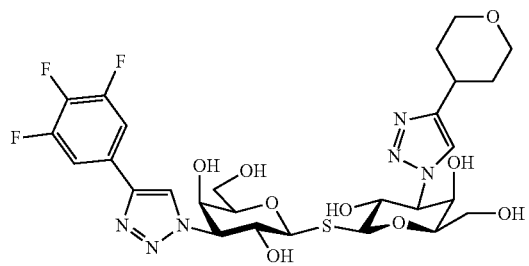

i1 (40 mg) and 4-ethynyltetrahydro-2H-pyran (35 mg) were dissolved in acetonitrile (4 mL) and degassed (argon). Copper(I) iodide (4 mg) was added followed by DIEA (100 μL). The mixture was stirred at r.t. overnight and then concentrated in vacuo and purified by HPLC (C$_{18}$/MeCN:H$_2$O:0.1% TFA). Freezedrying afforded a white fluffy solid (45 mg). $^1$H NMR (400 MHz, Methanol-d$_4$) δ 8.56 (s, 1H), 8.00 (s, 1H), 7.60 (dd, J=8.5, 6.5 Hz, 2H), 4.93-4.85 (m, 2H), 4.85-4.65 (m, 4H), 4.12 (dd, J=8.5, 2.7 Hz, 2H), 3.99 (d, J=11.8 Hz, 2H), 3.83 (ddt, J=18.0, 11.0, 6.4 Hz, 4H), 3.70 (dd, J=11.1, 4.0 Hz, 2H), 3.56 (t, J=11.4 Hz, 2H), 3.02 (s, 1H), 1.95 (d, J=13.1 Hz, 2H), 1.84-1.73 (m, 2H). ESI-MS calcd for [C$_{27}$H$_{34}$F$_3$N$_6$O$_9$S]$^+$ (M+H)$^+$: 675.20; found: 675.15.

Example 5

3,3'-Dideoxy-3-[4-(propan-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside

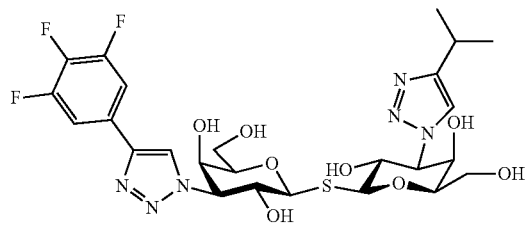

i2 (50 mg) was dissolved in MeCN (7 mL, dry) and 3-methylbut-1-yne (20 μL) was added and the mixture was stirred at r.t. under argon. Copper(I) iodide (14 mg) was added followed by Hünig's base (25 μL) and the mixture was heated to 27° C. After 18 h the mixture was concentrated down and purified by flash chromatography (SiO$_2$/Petroleum ether:EtOAc 95:5→5:95). The residue was dissolved in MeOH (10 mL, dry) and NaOMe (1M in MeOH, 0.50 mL) was added and the mixture was stirred at r.t. After 2 h HOAc (1 mL) was added and the mixture was concentrated down. The residue was purified by HPLC (C$_{18}$/MeCN:H$_2$O: 0.1% TFA). Freezedrying afforded a white fluffy solid (8 mg). $^1$H NMR (400 MHz, Methanol-d$_4$) δ 8.56 (s, 1H), 7.97 (s, 1H), 7.64-7.57 (m, 2H), 4.93-4.64 (m, 6H), 4.12 (dd, J=5.4, 2.8 Hz, 2H), 3.91-3.76 (m, 4H), 3.70 (dd, J=10.8, 3.7 Hz, 2H), 3.07 (p, J=6.8 Hz, 1H), 1.31 (dd, J=6.9, 2.6 Hz, 6H). ESI-MS calcd for [C$_{25}$H$_{32}$F$_3$N$_6$O$_8$S]$^+$ (M+H)$^+$: 633.19; found: 633.15.

Synthesis of Intermediates i1 and i2 via Steps b1-b2;

b1) 3-Azido-3,3'-dideoxy-3'-[4-(3,4,5-trifluorophenyl)-1H-1,2,3-triazol-1-yl]-1,1'-sulfanediyl-di-β-D-galactopyranoside (i1)

2,2',4,4',5,5',6,6'-Hexa-O-acetyl-3,3'-diazido-3,3'-dideoxy-1,1'-sulfanediyl-di-β-D-galactopyranoside (131 mg) and trimethyl-[2-(3,4,5-trifluorophenyl)ethynyl]silane (45 μl) were mixed in acetonitrile (5 mL) and degassed (argon). Cesium fluoride (30 mg) was added and the mixture stirred 5 min. Copper(I) iodide (4 mg) was added, followed by Hünig's base (100 μl). The mixture was stirred at r.t. overnight and then concentrated in vacuo. It was then evaporated on to silica and purified by flash chromatography (SiO$_2$/Petroleum ether:EtOAc 95:5→5:95).The appropriate fractions were concentrated and the residue dissolved in methanol (10 mL). 1M sodium methoxide in methanol (1.5 ml) was added and the mixture stirred 2 h. TFA (0.2 ml) was added and the mixture concentrated in vacuo. The residue was purified by HPLC (C$_{18}$/MeCN:H$_2$O:0.1% TFA). Freezedrying afforded Intermediate 1 (i1) as a white solid (61 mg).

b2) 2,2',4,4',5,5',6,6'-Hexa-O-acetyl-3-azido-3,3'-dideoxy-3'-[4-(3,4,5-trifluoroohenyl)-1H-1,2,3-triazol-1-yl]-1,1'-sulfanediyl-di-β-D-galactoovranoside (i2)

i1 (150 mg) was dissolved in pyridine (5 mL). Acetic anhydride (0.50 mL) was added and mixture stirred overnight and then concentrated in vacuo. The residue was dissolved in CH$_2$Cl$_2$ and filtered through silica (2 g), eluted with 2% MeOH in DCM. The filtrate was concentrated in vacuo to afford intermediate 2 (i2) as a white solid (209 mg). $^1$H NMR (400 MHz, Methanol-d$_4$) δ 8.58 (d, J=1.2 Hz, 2H), 7.60 (dd, J=8.5, 6.5 Hz, 4H), 4.90 (d, J=3.3 Hz, 4H), 4.72 (t, J=10.1 Hz, 2H), 4.16 (d, J=2.8 Hz, 2H), 3.94 - 3.78 (m, 4H), 3.72 (dd, J=11.3, 4.4 Hz, 2H).

i2 could optionally be made via step b3-b7;

b3) 2,4,6-Tri-O-acetyl-3-azido-3-deoxy-α-D-galactopyranosyl bromide 1,2,4,6-Tetra-O-acetyl-3-azido-3-deoxy-β-D-galactopyranoside (1.99 g) and titanium tetrabromide (2.7 g) were mixed in EtOAc (100 ml) and stirred at 27° C. 48 h. Washed with aq. 5% NaHCO$_3$ (100 ml) and brine (100 ml). Purification by flash chromatography (SiO$_2$/Petroleum ether:EtOAc 95:5→5:95) afforded 2.01 g of 2,4,6-tri-O-acetyl-3-azido-3-deoxy-α-D-galactopyranosyl bromide. $^1$H NMR (400 MHz, Chloroform-d) δ 6.71 (d, J=3.8 Hz, 1H), 5.50 (d, J=2.5 Hz, 1H), 4.95 (dd, J=10.6, 3.8 Hz, 1H), 4.42 (t, J=6.4 Hz, 1H), 4.22-4.03 (m, 3H), 2.18 (s, 3H), 2.17 (s, 3H), 2.08 (s, 3H).

b4) Tri-isopropylsilyl 2,4,6-tri-O-acetyl-3-azido-3-deoxy-1-thio-β-D-galactopyranoside 2,4,6-Tri-O-acetyl-3-azido-3-deoxy-α-D-galactopyranosyl bromide (370 mg) was dissolved in MeCN (15 mL, dry) and stirred at r.t. under argon for five minutes. K$_2$CO$_3$ (390 mg, dry) was added followed by TIPSSH (305 μL). After 200 minutes the mixture was concentrated down, re-dissolved in CH$_2$Cl$_2$ and washed twice with water. The water phase was extracted once with CH$_2$Cl$_2$ and the combined organic phase was dried (phase separator) and concentrated. Purification by flash chromatography (SiO$_2$/Petroleum ether:EtOAc 100:0→50:50) afforded 312 mg of tri-isopropylsilyl 2,4,6-tri-O-acetyl-3-azido-3-deoxy-1-thio-β-D-galactopyranoside. $^1$H NMR (400 MHz, Chloroform-d) δ 5.45 (d, J=2.5 Hz, 1H), 5.23 (t, J=9.8 Hz, 1H), 4.63 (d, J=9.5 Hz, 1H), 4.14 (dd, J=11.5, 5.5 Hz, 1H), 4.03 (dd, J=11.5, 7.2 Hz, 1H), 3.82 (t, J=6.3 Hz, 1H), 3.56 (dd, J=10.1, 3.3 Hz, 1H), 2.18 (s, 3H), 2.15 (s, 3H), 2.05 (s, 3H), 1.32-1.23 (m, 3H), 1.18-1.06 (m, 18H).

b5) 1,2,4,6-Tetra-O-acetyl-3-deoxy-3-[4-(3,4,5-trifluorophenyl)-1H-1,2,3-triazol-1-yl]-β-D-galactopyranoside Trimethyl-[2-(3,4,5-trifluorophenyl)ethynyl]silane (1120 μL) was dissolved in MeCN (50 mL, dry) and stirred at r.t. under argon and triethylamine trihydrofluoride (435 μL) was added. After 25 minutes 1,2,4,6-tetra-O-acetyl-3-azido-3-deoxy-β-D-galactopyranoside (1025 mg) was added followed by copper(I) iodide (138 mg) and Hünig's base (2.00 mL). After 18 h brine was added and the mixture was extracted three times with ether. The organic phase was washed once with brine, dried (Na$_2$SO$_4$) and concentrated. Re-crystallization from EtOH afforded 1.19 g of 1,2,4,6-tetra-O-acetyl-3-deoxy-3-[4-(3,4,5-trifluorophenyl)-1H-1,2,3-triazol-1-yl]-β-D-galactopyranoside. $^1$H NMR (400 MHz, Chloroform-d) δ 7.80 (s, 1H), 7.47-7.38 (m, 2H), 5.86 (d, J=9.1 Hz, 2H), 5.58 (s, 1H), 5.19 (d, J=9.2 Hz, 1H), 4.30-4.08 (m, 3H), 2.18 (s, 3H), 2.08 (s, 3H), 2.06 (s, 3H), 1.91 (s, 3H). ESI-MS m/z calcd for [C$_{22}$H$_{23}$F$_3$N$_3$O$_9$]$^+$ (M+H)$^+$:530.1; found: 530.1.

b6) 2,4,6-Tri-O-acetyl-3-deoxy-3-[4-(3,4,5-trifluorophenyl)-1H-1,2,3-triazol-1-yl]-α-D-galactopyranosyl bromide 1,2,4,6-tetra-O-acetyl-3-deoxy-3-[4-(3,4,5-trifluorophenyl)-1H-1,2,3-triazol-1-yl]-β-D-galactopyranoside (273 mg) was suspended in CH$_2$Cl$_2$/AcOH (1:1, 4 mL) and stirred at r.t. Acetic anhydride (1 mL) was added followed by HBr (33% in AcOH, 2 mL). After 20 h excess HBr was purged away with argon and the mixture was concentrated. Purification by flash chromatography (SiO$_2$/Petroleum ether:EtOAc 95:5→5:95) afforded 263 mg of 2,4,6-tri-O-acetyl-3-deoxy-3-[4-(3,4,5-trifluorophenyl)-1H-1,2,3-triazol-1-yl]-α-D-galactopyranosyl bromide. $^1$H NMR (400 MHz, Chloroform-d) δ 7.79 (s, 1H), 7.49-7.40 (m, 2H), 6.89 (d, J=3.8 Hz, 1H), 5.82 (dd, J=11.4, 3.9 Hz, 1H), 5.63 (s, 1H), 5.32 (d, J=11.2 Hz, 1H), 4.65 (t, J=6.5 Hz, 1H), 4.25 (dd, J=11.7, 6.3 Hz, 1H), 4.15 (dd, J=11.9, 6.4 Hz, 1H), 2.07 (s, 6H), 1.97 (s, 3H). ESI-MS m/z calcd for [$C_{20}H_{20}BrF_3N_3O_7$]$^+$ (M+H)$^+$:550.0; found: 550.0.

b7) 2,2',4,4',5,5',6,6'-Hexa-O-acetyl-3-azido-3,3'-dideoxy-3'-[4-(3,4,5-trifluorophenyl)-1H-1,2,3-triazol-1-yl]-1,1'-sulfanediyl-di-β-D-galactopyranoside (i2)

Tri-isopropylsilyl 2,4,6-tri-O-acetyl-3-azido-3-deoxy-1-thio-β-D-galactopyranoside (308 mg) was dissolved in MeCN (10 mL, dry) and stirred at r.t. under argon. 2,4,6-Tri-O-acetyl-3-deoxy-3-[4-(3,4,5-trifluorophenyl)-1H-1,2,3-triazol-1-yl]-α-D-galactopyranosyl bromide (405 mg) dissolved in MeCN (10 mL, dry) was added. After five minutes TBAF (235 mg) dissolved in MeCN (5 mL, dry) was added. After two minutes the mixture was cooled to 0° C. and after another three minutes the mixture was concentrated. Purification by flash chromatography (SiO$_2$/Petroleum ether: EtOAc 100:0→0:100) afforded 262 mg of 2,2',4,4',5,5',6,6'-hexa-O-acetyl-3-azido-3,3'-dideoxy-3'-[4-(3,4,5-trifluorophenyl)-1H-1,2,3-triazol-1-yl]-1,1'-sulfanediyl-di-β-D-galactopyranoside. $^1$H NMR (400 MHz, Chloroform-d) δ 7.83 (s, 1H), 7.47-7.41 (m, 2H), 5.74 (t, J=10.4 Hz, 1H), 5.62 (d, J=2.4 Hz, 1H), 5.51 (d, J=2.3 Hz, 1H), 5.24 (t, J=10.0 Hz, 2H), 5.17 (dd, J=10.9, 3.1 Hz, 1H), 4.97 (d, J=9.8 Hz, 1H), 4.83 (d, J=9.9 Hz, 1H), 4.21 (dt, J=21.3, 5.6 Hz, 6H), 4.15-4.07 (m, 2H), 3.92 (t, J=6.4 Hz, 1H), 3.68 (dd, J=10.0, 3.3 Hz, 1H), 2.20 (s, 3H), 2.17 (s, 3H), 2.12 (s, 3H), 2.09 (s, 3H), 2.07 (s, 3H), 1.93 (s, 3H). ESI-MS calcd for [$C_{32}H_{36}F_3N_6O_{14}S$]$^+$ (M+H)$^+$:817.2; found: 817.2.

Study of Ocular Fibrosis in Rabbits

30 New Zealand white rabbits were housed in metal cages that conformed to standards set forth in the Animal Welfare Act and the Guide for the Care and Use of Laboratory Animals. Space recommendations for animals were in accordance with PHS policy and the AWA.

Animals were fed food that was fresh, palatable and nutritionally adequate ad libitum. Filtered tap water or spring water (non-acidified) was provided ad libitum.

Environmental controls were set to maintain temperatures 18±2° C. (65±2° F.) with relative humidity between 50±20%. A 12-hour light/dark cycle was maintained.

The animals were acclimated for at least 5 days after arrival at the facility prior to study procedures.

The vehicle gel formulation was 1.65% (w/v) HEC in NaCl. The vehicle formulation was prepared by adding the appropriate amount of HEC to 75% of the required volume of 0.9% NaCl. The resulting formulation was stirred for 20 to 25 minutes after which it was QS'ed (adjusted) to the final volume with 0.9% NaCl and stirred for an additional 2 to 3 hours at room temperature. The gel formulation was then filtered with a 0.2 μm cellulose filter.

The test item formulations were prepared by adding the appropriate amount of GB1A or GB1B to 75% of the required volume of 0.9% NaCl. The resulting formulation was agitated for 20 to 25 minutes after which the pH of the solution was measured and adjusted, as necessary, to 6-6.5 with 0.01M NaOH. The required amount of HEC was added to the test item solution and the formulation was agitated for 20 to 25 minutes. The formulation was then QS'ed to the final volume with NaCl and agitated for an additional 2 to 3 hours at room temperature. The final gel formulation was filtered with a 0.2 μm cellulose filter.

Retinal detachments were created by infusing a dilute solution (0.25%) of Healon into the subretinal space of the right eyes in 30 New Zealand White rabbits. Fifty (50) μL of GB1A (0.05 mg/mL), GB1B (1.5 mg/mL), or vehicle (HEC) formulations were injected intravitreally immediately after the detachment surgery in the right eyes of all animals (n=5 for each vehicle/test item at each time-point). The left eyes served as naïve controls. Euthanasia was performed by administering "Euthasol" IV via an ear vein, on animals of Groups 1 to 3, 3 days after retinal detachment (n=15) to examine the effects on proliferation, and on animals of Groups 4 to 6, 7 days after retinal detachment (n=15) to examine the effects on scaring.

Following euthanasia, the retinas were fixed in 4% paraformaldehyde for 24 hours. Three retinal regions approximately 3 mm square were sampled from within each detached retina as well as from control retinas. The retinas were embedded in agarose and vibratomed at 100 microns in thickness. Sections were immunolabeled with antibodies to intermediate filament proteins (vimentin) and proliferating cells (Ki67). A marker for immune cells (Isolectin B4) and a nuclear stain (DAPI) was also used. All 4 probes were added to the same sections (i.e. quadruple labeling).

The sections were imaged using an Olympus FV1000 confocal microscope. Digital images were acquired and used to determine 1) the number and size of subretinal glial scars 2) the number of dividing cells and their cell type e.g. of immune or glial origin 3) whether microglia are "activated" and 4) if macrophages are present. Animals were weighed pre-dose and at euthanasia. All animals gained a small amount of weight as was expected.

Eyes were examined once a day after surgery until termination of the experiment.

TABLE 1

Group Assignment

| Group | Number of Animals | Route of Administration | Dose Volume (uL/eye) | Concentration (mg/mL) | Termination Day |
|---|---|---|---|---|---|
| 1. Vehicle | 5 | IVT | 50 | 0 | Day 3 |
| 2. GB1A | 5 | IVT | 50 | 0.05 | Day 3 |
| 3. GB1B | 5 | IVT | 50 | 1.5 | Day 3 |
| 4. Vehicle | 5 | IVT | 50 | 0 | Day 7 |
| 5. GB1A | 5 | IVT | 50 | 0.05 | Day 7 |
| 6. GB1B | 5 | IVT | 50 | 1.5 | Day 7 |

Animals were euthanized with sodium pentobarbital (Euthasol®) at a dose level of 200-500 mg/kg administered by IV injection (through ear catheter or direct in the marginal ear vein) following anesthetization with Ketamine/Xylazine (~35 mg/kg/~5 mg/kg by IM injection). Monitoring for the absence of a heart beat for at least 60 seconds, as well as a lack of eye and pedal reflexes, were performed in accordance with accepted American Veterinary Medical Association (AVMA) guidelines.

Following euthanasia, the eyes were enucleated, the cornea and lens removed and the eyecups fixed in 4% paraformaldehyde in PBS for 24 hours. Three retinal regions approximately 3 mm$^2$ were dissected from within each detached retina and embedded in agarose for sectioning as described above. Following immunolabeling, the sections were mounted on glass slides and cover-slipped. Digital images were captured from along the length of each section collected from each of the 3 retinal regions using a FV1000 confocal microscope. Quantitation of scar length and number, as well as the number of dividing cells, was performed using the digital images viewed in "BioImage" (software available as a free download from UCSB's dept. of engineering). In addition, the presence of immune cells as described in the Experimental Design was noted and tabulated for each animal.

Seven days after retinal detachment, the control (HEC-treated) retinas had 1.26 scars per mm of retina with an average length of 175 microns per mm of retina. Following treatment with GB1B, the number decreased to 0.43 scars per mm of retina (p=0.0071), and the length was reduced to 28.8 microns per mm of retina (p=0.0165). Following treatment with GB1A, the number decreased to 0.45 scars per mm of retina (p=0.0143), and the length was reduced to 25.83 microns per mm of retina (p=0.0142). The treated groups were significantly different from the controls for both test items.

Three days after retinal detachment, the control (HEC-treated) retinas had 9.57 Ki67 labeled Muller cells per mm of retina. Following treatment with GB1B, this number was reduced to 2.73 cells per mm of retina (P=0.0052), while treatment with GB1A reduced it to 3.01 (P=0.009).

It has previously been shown that within one day following retinal detachment, Muller cells begin to proliferate, and this response peaks at Day 3 after detachment in the rabbit retina and declines to very low levels after that. (cf. S. F Geller et al., 1995, IOVS, 36:737-744). Concomitant with this response, the Muller cells also begin to hypertrophy and expand their area of cytoplasm, as can be visualized using antibodies to intermediate filament proteins (e.g. GFAP or vimentin). This hypertrophy does not result in subretinal scaring at day 3, but by Day 7 in the rabbit retina, it results in the growth of the Muller cells into the subretinal space. This scaring is highly detrimental to the recovery of vision since it inhibits the regeneration of photoreceptor outer segments, and the reapposition to the RPE following reattachment surgery.

It has been demonstrated that both GB1A and GB1B in HEC formulation were highly effective at reducing the size and number of subretinal glial scars as well as the number of dividing cells, paving the way for potential new treatment strategies for scaring in the eye. Indeed, scars resulting from the growth and hypertrophy of Muller cells can be found in conditions such as subretinal fibrosis and epiretinal membrane formation in humans, as well as in diseases such as AMD, retinitis pigmentosa, and diabetic retinopathy.

REFERENCES

Aits S, Kricker J, Liu B, Ellegaard A M, Hämälistö S, Tvingsholm S, Corcelle-Termeau E, Høgh S, Farkas T, Holm Jonassen A, Gromova I, Mortensen M, Jaattela M. (2015) Sensitive detection of lysosomal membrane permeabilization by lysosomal galectin puncta assay Autophagy. 2015; 11(8):1408-24.

Arthur C M, Baruffi M D, Cummings R D, Stowell S R. (2015) Evolving mechanistic insights into galectin functions. Methods Mol Biol. 1207:1-35.

Blanchard H, Yu X, Collins P M, Bum-Erdene K. (2014) Galectin-3 inhibitors: a patent review (2008-present). Expert Opin Ther Pat. 2014 October; 24(10):1053-65.

Blidner A G, Méndez-Huergo S P, Cagnoni A J, Rabinovich G A. (2015) Re-wiring regulatory cell networks in immunity by galectin-glycan interactions. FEBS Lett. 2015 Sep. 6. pii: 50014-5793(15)00807-8.

Chen, W.-S., Leffler H., Nilsson, U. J., Panjwani, N. (2012). Targeting Galectin-1 and Galectin-3 Attenuates VEGF-A-induced Angiogenesis; Mol. Biol. Cell (suppl), Abstract No. 2695.

Clare D K, Magescas J, Piolot T, Dumoux M, Vesque C, Pichard E, Dang T, Duvauchelle B, Poirier F, Delacour D. (2014) Basal foot MTOC organizes pillar MTs required for coordination of beating cilia. Nat Commun. 5:4888.

Croci D O, Cerliani J P, Pinto N A, Morosi L G, Rabinovich G A. (2014) Regulatory role of glycans in the control of hypoxia-driven angiogenesis and sensitivity to anti-angiogenic treatment. Glycobiology. 2014 December; 24(12):1283-90.

Cumpstey, I., Carlsson, S., Leffler, H. and Nilsson, U. J. (2005) Synthesis of a phenyl thio-β-D-galactopyranoside library from 1,5-difluoro-2,4-dinitrobenzene: discovery of efficient and selective monosaccharide inhibitors of galectin-7. Org. Biomol. Chem. 3: 1922-1932.

Cumpstey, I., Sundin, A., Leffler, H. and Nilsson, U. J. (2005) $C_2$-Symmetrical thiodigalactoside bis-benzamido derivatives as high-affinity inhibitors of galectin-3: Efficient lectin inhibition through double arginine-arene interactions. Angew. Chem. Int. Ed. 44: 5110-5112.

Cumpstey, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. Chem. Eur. J. 14: 4233-4245.

Delaine, T.; Collins, P., Mac Kinnon, A., Sharma, G., Stegmayr, J., Rajput, V. K., Mandal, S.; Cumpstey, I., Larumbe, A., Salameh, B. A., Kahl-Knutsson, B., van Hattum, H., van Scherpenzeel, M., Pieters, R. J., Sethi, T., Schambye, H., Oredsson, S., Leffler, H.; Blanchard, H., Nilsson, U. ChemBioChem 2016, 1-15.

Demotte, N., Wieers, G., van der Smissen, P., Moser, M., Schmidt, C., Thielemans, K., et al., (2010). Cancer Res. 70; 7476-7488.

Ebrahim A H, Alalawi Z, Mirandola L, Rakhshanda R, Dahlbeck S, Nguyen D, Jenkins M I, Grizzi F, Cobos E, Figueroa J A, Chiriva-Internati M (2014Galectins in cancer: carcinogenesis, diagnosis and therapy. Ann Transl Med. 2014 September; 2(9):88.

Elola M T, Blidner A G, Ferragut F, Bracalente C, Rabinovich G A. (2015) Assembly, organization and regulation of cell-surface receptors by lectin-glycan complexes. Biochem J. 2015 Jul. 1; 469(1):1-16.

Funasaka T, Raz A, Nangia-Makker P. (2014) Nuclear transport of galectin-3 and its therapeutic implications. Semin Cancer Biol. 2014 August; 27:30-8.

Glinsky, G. V., Price, J. E., Glinsky, V. V., Mossine, V. V., Kiriakova, G., and Metcalf, J. B. (1996). Cancer Res 56: 5319-5324.

Glinsky V V, Raz A. (2009) Modified citrus pectin anti-metastatic properties: one bullet, multiple targets. Carbohydr Res. 344(14):1788-91.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Breast *Cancer. Clin. Cancer Res.* 9: 2374-2383.

Kouo, T., Huang, L., Pucsek, A. B., Cao, M., Solt, S., Armstrong, T., Jaffee, E. (2015) *Cancer Immonol. Res.* 3: 412-23

Li L C, Li J, Gao J. (2014) Functions of galectin-3 and its role in fibrotic diseases. J
Pharmacol Exp Ther. 2014 November; 351(2):336-43.

Leffler, H., Carlsson, S., Hedlund, M., Qian, Y. and Poirier, F. (2004) Introduction to galectins. *Glycoconj. J.* 19: 433-440.

Lepur A, Salomonsson E, Nilsson U J, Leffler H. (2012) Ligand induced galectin-3 protein self-association. J Biol Chem. 2012 Jun. 22; 287(26):21751-6.

MacKinnon, A. C., Farnworth, S. L., Henderson, N. C., Hodkinson, P. S., Kipari, T., Leffler, H., Nilsson, U. J., Haslett, C., Hughes, J., and Sethi T. (2008). Regulation of alternative macrophage activation by Galectin-3. *J. Immun.* 180; 2650-2658.

Mackinnon, A., Gibbons, M., Farnworth, S., Leffler, H., Nilsson, U. J., Delaine, T., Simpson, A., Forbes, S., Hirani, N., Gauldie, J., and Sethi T. (2012). Regulation of TGF-β1 driven lung fibrosis by Galectin-3. *Am. J. Resp. Crit. Care Med.,* 185; 537.

Melero, I., Berman, D. M., Aznar, M. A., Korman, A. J., Gracia, J. L. P., Haanen, J. (2015) *Nature Reviews Cancer,* 15: 457-472

Ruvolo, P. P. *Biochim. Biophys Acta*. Molecular cell research (2015) E-pub ahead of print, title: Galectin 3 as a guardian of the tumor microenvironment, published on-line 8 Apr. 2015: (http://www.sciencedirect.com/science/article/pii/S0167488915002700), Salameh, B. A., Leffler, H. and Nilsson, U. J. (2005) *Bioorg. Med. Chem. Lett.* 15: 3344-3346.

Salameh, B. A., Cumpstey, I., Sundin, A., Leffler, H., and Nilsson, U. J. (2010). 1H-1,2,3-Triazol-1-yl thiodigalactoside derivatives as high affinity galectin-3 inhibitors. *Bioorg Med Chem* 18: 5367-5378.

Salomonsson, E., Larumbe, A., Tejler, J., Tullberg, E., Rydberg, H., Sundin, A., Khabut, A., Frejd, T., Lobsanov, Y. D., Rini, J. M., Nilsson, U. J., and Leffler, H (2010). Monovalent interactions of galectin-1. *Biochemistry* 49: 9518-9532.

Sörme, P., Qian, Y., Nyholm, P.-G., Leffler, H., Nilsson, U. J. (2002) Low micromolar inhibitors of galectin-3 based on 3'-derivatization of N-acetyllactosamine *ChemBioChem* 3:183-189.

Sörme, P., Kahl-Knutsson, B., Wellmar, U., Nilsson, U. J., and Leffler H. (2003a)
Fluorescence polarization to study galectin-ligand interactions. *Meth. Enzymol.*362: 504-512.

Sörme, P., Kahl-Knutsson, B., Wellmar, U., Magnusson, B.-G., Leffler H., and Nilsson, U. J. (2003b) Design and synthesis of galectin inhibitors. *Meth. Enzymol.*363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* 334: 36-47.

Thijssen V L, Heusschen R, Caers J, Griffioen A W. (2015) Galectin expression in cancer diagnosis and prognosis: A systematic review. Biochim Biophys Acta. 2015 April; 1855(2):235-47.

Viguier M, Advedissian T, Delacour D, Poirier F, Deshayes F. (2014) Galectins in epithelial functions. Tissue Barriers. 2014 May 6; 2:e29103.

Wolfenden M, Cousin J, Nangia-Makker P, Raz A, Cloninger M. (2015) Glycodendrimers and Modified ELISAs: Tools to Elucidate Multivalent Interactions of Galectins 1 and 3. Molecules. 2015 Apr. 20; 20(4):7059-96.

We claim:

1. A 1,1'-sulfanediyl-di-β-D-galactopyranoside compound of formula (1)

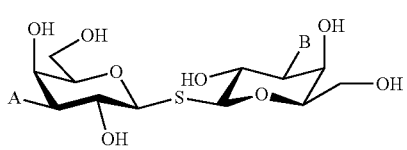

wherein A is a group of formula 2

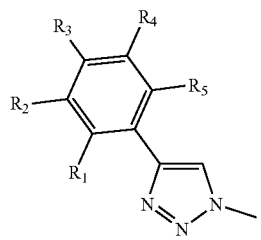

wherein $R_1$-$R_5$ are independently selected from the group consisting of: H; Cl; Br; I; F; methyl optionally substituted with one or more fluorine atoms (F); $R_7O$—, wherein $R_7$ is a $C_{1-3}$ alkyl optionally substituted with one or more F; $NH_2$; OH; CN; $NH_2$—$COR_8$, wherein $R^8$ is selected from $C_{1-3}$ alkyl optionally substituted with one or more F; and $OCH_3$ optionally substituted with one or more F; and B is a group of formula 3

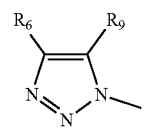

wherein $R_6$ is either a branched $C_{3-6}$ alkyl or a 6-membered heterocyclic group being saturated and having 1-2 hetero atoms and 3-5 carbon atoms, optionally substituted with a $C_{1-4}$- alkyl, and wherein $R_9$ is selected from the group consisting of:
H; Cl; Br; I; F; $NR_{10}R_{11}$; $OR_{12}$; C(=O)—$R_{13}$; CN; O(C=O)—$R_{16}$; NH(C=O)—$R_{17}$; C(=O)—$OR_{21}$; C(=O)—$NR_{22}R_{23}$; $SR_{18}$; S(=O)—$R_{19}$; $SO_2R_{20}$;
a $C_{1-10}$ alkyl, optionally substituted with one or more: F; Oxo; $NR_{14}R_{15}$; $OR_{24}$; C(=O)—$R_{25}$; CN; O(C=O)—$R_{26}$; NH(C=O)—$R_{27}$; C(=O)—$OR_{28}$; C(=O)—$NR_{29}R_{30}$; $SR_{31}$; S(=O)—$R_{32}$; or $SO_2R_{33}$;

a $C_{3-7}$ cycloalkyl, optionally substituted with one or more: F; Oxo; $NR_{34}R_{35}$; $OR_{36}$; $C(=O)-R_{37}$; CN; $O(C=O)-R_{38}$; $NH(C=O)-R_{39}$; $C(=O)-OR_{40}$; $C(=O)-NR_{41}R_{42}$; $SR_{43}$; $S(=O)-R_{44}$; $SO_2R_{45}$; or $C_{1-4}$ alkyl optionally substituted with one or more F;

a branched $C_{3-10}$ alkyl, optionally substituted with one or more: F; Oxo; $NR_{46}R_{47}$; $OR_{48}$; $C(=O)-R_{49}$; CN; $O(C=O)-R_{50}$; $NH(C=O)-R_{51}$; $C(=O)-OR_{52}$; $C(=O)-NR_{53}R_{54}$; $SR_{55}$; $S(=O)-R_{56}$; $SO_2R_{57}$; or a $C_{1-4}$ alkyl optionally substituted with F; and a 4-7-membered heterocyclic group being saturated or unsaturated and having 1-3 hetero atoms and 3-6 carbon atoms, optionally substituted with a $C_{1-4}$ alkyl optionally substituted with one or more: F; Oxo; $NR_{58}R_{59}$; $OR_{60}$; $C(=O)-R_{61}$; CN; $O(C=O)-R_{62}$; $NH(C=O)-R_{63}$, $SR_{64}$; $S(=O)-R_{65}$; or $SO_2R_{66}$;

wherein $R_{10}$-$R_{66}$ are independently selected from the group consisting of:

H;

a $C_{1-10}$ alkyl optionally substituted with one or more: F; oxo; CN; $OCH_3$; $OCF_3$; $OCH_2CH_3$, optionally substituted with one or more F, and $SCH_2CH_3$, optionally substituted with one or more F, $SCH_3$, $SCF_3$, $OCH_3$, or $OCF_3$;

a $C_{3-7}$ cycloalkyl optionally substituted with one or more: F; oxo; CN; $OCH_3$; $OCF_3$; $OCH_2CH_3$, optionally substituted with one or more F; and $SCH_2CH_3$, optionally substituted with one or more F, $SCH_3$, $SCF_3$, $OCH_3$, or $OCF_3$;

a branched $C_{3-10}$ alkyl, optionally substituted with one or more: F; oxo; CN; $OCH_3$; $OCF_3$; $OCH_2CH_3$, optionally substituted with one or more F; and $SCH_2CH_3$, optionally substituted with one or more F, $SCH_3$, $SCF_3$, $OCH_3$, or $OCF_3$;

a 4-7-membered heterocyclic group being saturated or unsaturated and having 1-3 hetero atoms and 3-6 carbon atoms optionally substituted with one or more: F; oxo; CN; $OCH_3$; $OCF_3$; $OCH_2CH_3$, optionally substituted with one or more F; and $SCH_2CH_3$, optionally substituted with one or more F, $SCH_3$, $SCF_3$, $OCH_3$, or $OCF_3$;

a $OC_{1-10}$ alkyl optionally substituted with one or more: F; oxo; CN; $OCH_3$; $OCF_3$; $OCH_2CH_3$, optionally substituted with one or more F; and $SCH_2CH_3$, optionally substituted with one or more F, $SCH_3$, $SCF_3$, $OCH_3$, or $OCF_3$;

a $OC_{3-7}$ cycloalkyl optionally substituted with one or more: F; oxo; CN; $OCH_3$; $OCF_3$; $OCH_2CH_3$, optionally substituted with one or more F; and $SCH_2CH_3$, optionally substituted with one or more F, $SCH_3$, $SCF_3$, $OCH_3$, or $OCF_3$;

a O-(4-7-membered heterocyclic group being saturated or unsaturated and having 1-3 hetero atoms and 3-6 carbon atoms) optionally substituted with one or more: F; oxo; CN; $OCH_3$; $OCF_3$; $OCH_2CH_3$, optionally substituted with one or more F; and $SCH_2CH_3$, optionally substituted with one or more F, $SCH_3$, $SCF_3$, $OCH_3$, or $OCF_3$;

a $NHC_{1-10}$ alkyl optionally substituted with one or more: F; oxo; CN; $OCH_3$; $OCF_3$; $OCH_2CH_3$, optionally substituted with one or more F; and $SCH_2CH_3$, optionally substituted with one or more F, $SCH_3$, $SCF_3$, $OCH_3$, or $OCF_3$;

a $NHC_{3-7}$ cycloalkyl optionally substituted with one or more: F; oxo; CN; $OCH_3$; $OCF_3$; $OCH_2CH_3$, optionally substituted with one or more F; and $SCH_2CH_3$, optionally substituted with one or more F, $SCH_3$, $SCF_3$, $OCH_3$, or $OCF_3$; and a NH-(4-7-membered heterocyclic group being saturated or unsaturated and having 1-3 hetero atoms and 3-6 carbon atoms) optionally substituted with one or more: F; oxo; CN; $OCH_3$; $OCF_3$; $OCH_2CH_3$, optionally substituted with one or more F; or $SCH_2CH_3$, optionally substituted with one or more F, $SCH_3$, $SCF_3$, $OCH_3$, or $OCF_3$;

or a pharmaceutically acceptable salt or solvate thereof.

2. The compound of claim 1, wherein $R_1$ is H or F.

3. The compound of claim 1, wherein $R_2$ is H or F.

4. The compound of claim 1, wherein $R_3$ is H or F.

5. The compound of claim 1, wherein $R_4$ is H or F.

6. The compound of claim 1, wherein $R_5$ is H or F.

7. The compound of claim 1, wherein $R_6$ is a branched $C_{3-6}$ alkyl.

8. The compound of claim 7, wherein $R_6$ is an iso-propyl group.

9. The compound of claim 1, wherein $R_6$ is a 6-membered heterocyclic group being saturated and having 1-2 hetero atoms and 3-5 carbon atoms, optionally substituted with a $C_{1-4}$ alkyl.

10. The compound of claim 1, wherein $R_6$ is selected from the group consisting of: a piperidinyl, piperazinyl, morpholinyl, and tetrahydropyranyl, optionally substituted with a $C_{1-4}$ alkyl.

11. The compound of claim 1, wherein $R_9$ is H.

12. The compound of claim 1, wherein the compound is selected from the group consisting of:

3,3'-Dideoxy-3-[4-(morpholin-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside, 3,3'-Dideoxy-3-[4-(4-methylpiperazin-1-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside, 3,3'-Dideoxy-3-[4-(piperidin-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside, 3,3'-Dideoxy-3-[4-(tetrahydropyran-4-yl)-1H-1,2,3-triazol-1-yl]-3'-[4(3,4,5-trifluorophenyl)-1H-1,2,3-triazol-1-yl]-1,1'-sulfanediyl-di-β-D-galactopyranoside, and 3,3'-Dideoxy-3-[4-(propan-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside.

13. A pharmaceutical composition comprising the compound of claim 1 and optionally a pharmaceutically acceptable additive.

14. The compound of claim 1, wherein $R_1$, $R_2$, $R_3$, $R_4$ and $R_5$ are each independently H or F.

15. The compound of claim 1, wherein $R_1$ and $R_5$ are each H and wherein $R_2$, $R_3$ and $R_4$ are each F.

16. A method for treating a disorder relating to the binding of a galectin to a ligand in a mammal, comprising administering a therapeutically effective amount of the compound of claim 1 to a mammal in need of said treatment.

17. The method of claim 16, wherein said disorder is selected from the group consisting of: inflammation; fibrosis; septic shock; cancer; autoimmune diseases; metabolic disorders; heart disease; heart failure; pathological angiogenesis; ocular angiogenesis; a disease or condition associated with ocular angiogenesis; neovascularization related to cancer; proliferative vitreoretinopathy; and eye diseases.

18. The method of claim 17, wherein the disorder is a fibrosis selected from the group consisting of pulmonary fibrosis, liver fibrosis, kidney fibrosis, ophtalmological fibrosis and fibrosis of the heart.

19. The method of claim 17, wherein the disorder is an eye disease selected from the group consisting of age-related macular degeneration and corneal neovascularization.

20. The method of claim 16, wherein the mammal is a human.

* * * * *